United States Patent
Hoffman et al.

(10) Patent No.: US 8,455,468 B2
(45) Date of Patent: *Jun. 4, 2013

(54) METHODS FOR THE TREATMENT OF A TRAUMATIC CENTRAL NERVOUS SYSTEM INJURY

(75) Inventors: Stuart W. Hoffman, Atlanta, GA (US); Arthur L. Kellermann, Atlanta, GA (US); Donald G Stein, Atlanta, GA (US); David W. Wright, Atlanta, GA (US); Douglas W. Lowery-North, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/045,180

(22) Filed: Mar. 10, 2011

(65) Prior Publication Data
US 2011/0224181 A1    Sep. 15, 2011

Related U.S. Application Data

(63) Continuation of application No. 12/117,217, filed on May 8, 2008, now Pat. No. 7,915,244, which is a continuation of application No. 11/527,816, filed on Sep. 27, 2006, now Pat. No. 7,473,687, which is a continuation-in-part of application No. PCT/US2006/010797, filed on Mar. 24, 2006.

(60) Provisional application No. 60/664,728, filed on Mar. 24, 2005, provisional application No. 60/729,663, filed on Oct. 24, 2005.

(51) Int. Cl.
*A61K 31/56* (2006.01)

(52) U.S. Cl.
USPC .............................. 514/170; 514/182

(58) Field of Classification Search
USPC ................................... 514/170, 182
See application file for complete search history.

(56) References Cited

U.S. PATENT DOCUMENTS

| | | | |
|---|---|---|---|
| 4,404,366 A | 9/1983 | Boguslaski et al. |
| 5,120,723 A | 6/1992 | Gee et al. |

(Continued)

FOREIGN PATENT DOCUMENTS

| | | |
|---|---|---|
| WO | WO 89/02272 | 3/1989 |
| WO | WO 94/23708 | 10/1994 |

(Continued)

OTHER PUBLICATIONS

Notice of Allowance issued on Aug. 11, 2008, by the Examiner in U.S. Appl. No. 11/527,816 (US 7,473,687).

(Continued)

*Primary Examiner* — San-Ming Hui
(74) *Attorney, Agent, or Firm* — Foley & Lardner LLP

(57) ABSTRACT

Methods of treating a subject with a traumatic central nervous system injury, more particularly, a traumatic brain injury, are provided. The methods comprise a therapy comprising a constant or a two-level dosing regime of progesterone. In one method, a subject in need thereof is administered at least one cycle of therapy, wherein the cycle of therapy comprises administering a therapeutically effective two-level intravenous dosing regime of progesterone. The two-level dosing regime comprises a first time period, wherein a higher hourly dose of progesterone is administered to the subject, followed by a second time period, wherein a lower hourly dose of progesterone is administered to the subject.

17 Claims, 5 Drawing Sheets

U.S. PATENT DOCUMENTS

| | | | |
|---|---|---|---|
| 5,206,415 | A | 4/1993 | Covey et al. |
| 5,212,167 | A | 5/1993 | Farb |
| 5,232,917 | A | 8/1993 | Bolger et al. |
| 5,292,906 | A | 3/1994 | Covey et al. |
| 5,344,826 | A | 9/1994 | Covey et al. |
| 5,366,968 | A | 11/1994 | Farb |
| 5,550,120 | A | 8/1996 | Jackson |
| RE35,517 | E | 5/1997 | Gee et al. |
| 5,633,011 | A | 5/1997 | Dong et al. |
| 5,728,688 | A | 3/1998 | Labrie |
| 5,763,431 | A | 6/1998 | Jackson |
| 5,763,492 | A | 6/1998 | Johnson et al. |
| 5,767,117 | A | 6/1998 | Moskowitz |
| 5,780,460 | A | 7/1998 | Labrie |
| 5,798,347 | A | 8/1998 | Labrie |
| 5,807,849 | A | 9/1998 | Labrie |
| 5,824,671 | A | 10/1998 | Labrie |
| 5,837,544 | A | 11/1998 | Capon et al. |
| 5,837,700 | A | 11/1998 | Labrie |
| 5,843,932 | A | 12/1998 | Labrie |
| 5,872,114 | A | 2/1999 | Labrie |
| 5,888,996 | A | 3/1999 | Farb |
| 5,922,700 | A | 7/1999 | Labrie |
| 5,925,630 | A | 7/1999 | Upasani et al. |
| 5,929,061 | A | 7/1999 | Moskowitz |
| 5,939,545 | A | 8/1999 | Upasani et al. |
| 5,942,241 | A | 8/1999 | Chasin et al. |
| 5,955,455 | A | 9/1999 | Labrie |
| 6,114,388 | A | 9/2000 | Geffard |
| 6,245,757 | B1 | 6/2001 | Chopp et al. |
| 7,473,687 | B2 | 1/2009 | Hoffman et al. |
| 7,915,244 | B2 | 3/2011 | Hoffman et al. |
| 2001/0001280 | A1 | 5/2001 | Dong et al. |
| 2002/0072509 | A1* | 6/2002 | Stein et al. ............. 514/169 |
| 2008/0318914 | A1 | 12/2008 | Hoffman et al. |
| 2009/0221544 | A1 | 9/2009 | Stein et al. |
| 2009/0325920 | A1 | 12/2009 | Hoffman et al. |

FOREIGN PATENT DOCUMENTS

| | | |
|---|---|---|
| WO | WO 97/43989 | 11/1997 |
| WO | WO 98/50042 | 11/1998 |
| WO | WO 02/30409 | 4/2002 |
| WO | WO 2006/102596 | 9/2006 |

OTHER PUBLICATIONS

Notice of Allowance issued on Feb. 8, 2008, by the Examiner in U.S. Appl. No. 11/527,816 (US 7,473,687).

Office Action issued on May 3, 2007, by the Examiner in U.S. Appl. No. 11/527,816 (US 7,473,687).

Office Action issued on Aug. 19, 2009, by the Examiner in U.S. Appl. No. 12/117,217 (US 2008/0318914).

International Search Report issued on Nov. 14, 2006 for application No. PCT/US2006/010984 (corresponding to US 2009/0221544).

International Search Report issued on Mar. 25, 2008 for application No. PCT/US2007/079655 (corresponding to US 7,473,687).

International Search Report issued on Nov. 14, 2006 for application No. PCT/US2006/010797 (Corresponding to US 2009/0325920).

Wright et al., "Steady-State Serum Concentrations of Progesterone Following Continuous Intravenous Infusion in Patients with Acute Moderate to Severe Traumatic Brain Injury," *J. Clin. Pharmacol.*, vol. 45, pp. 640-648 (2005).

Cutler et al., "Slow-Release and injected progesterone treatments enhance acute recovery after traumatic brain injury," *Pharmacology, Biochemistry and Behavior*, vol. 84, No. 3, pp. 420-428 (2006).

Cutler et al., "Tapered progesterone withdrawal promotes long-term recovery following brain trauma," *Experimental Neurology*, vol. 200, No. 2, pp. 378-385, Aug. 2006.

Cutler et al., "Tapered progesterone withdrawal enhances behavioral and molecular recover after traumatic brain injury," *Experimental Neurology*, vol. 195, No. 2, pp. 423-429 (Oct. 2005).

Guo et al., "Progesterone administration modulates AQP4 expression and edema after traumatic brain injury in male rats," *Experimental Neurology*, vol. 198, No. 2, pp. 469-478 (2006).

He et al., "Progesterone and allopregnanolone reduce inflammatory cytokines after traumatic brain injury," *Experimental Neurology*, vol. 189, No. 2, pp. 404-412 (2004).

Jones et al., "The neuroprotective effect of progesterone after traumatic brain injury in male mice is independent of both the inflammatory response and growth factor expression," *Euro Journal of Neuroscience*, vol. 21, No. 6, pp. 1547-1554 (2005).

O'Connor et al., "Both estrogen and progesterone attenuate edema formation following diffuse traumatic brain injury in rats," *Brain Research*, vol. 1062, No. 102, pp. 171-174 (2005).

Goss et al., "Behavioral effects and anatomic correlates after brain injury: A progesterone dose-response study," *Pharmacology, Biochemistry and Behavior*, vol. 76, No. 2, pp. 231-242, Sep. 2003.

Shear et al., "Progesterone protects against necrotic damage and behavioral abnormalities caused by traumatic brain injury," *Experimental Neurology*, vol. 178, No. 1, Nov. 2002.

Roberts et al., "Absence of evidence for the effectiveness of five interventions routinely used in the intensive care management of severe heads injury: a systematic review," *J. Neurol. Neurosurg. Psychiatry*, vol. 65, pp. 729-733, 1998.

Vink et al., "An overview of new and novel pharmacothereapies for use in traumatic brain injury," *Clinical and Experimental Pharmacology and Physiology*, vol. 28, pp. 919-921, 2001.

Faden et al., "Neuroprotection and traumatic brain injury: theoretical option or realistic proposition," *Curr. Opin. Neurol.*, vol. 15, pp. 707-712, 2002.

Narayan et al., "Clinical trials in head injury," *J. Neurotrauma*, vol. 19, No. 5, pp. 503-557, 2002.

Matz, "Clinical Trials for Traumatic Brain Injury: The road traveled and development of new pathways," *Seminars in Neurosurgery*, vol. 14, No. 2, pp. 139-146, 2003.

Doppenberg et al., "Clinical Trials in Traumatic Brain Injury: Lessons for the Future," *J. Neurosurg. Anesthesiol*, vol. 16, No. 1, pp. 87-94, 2004.

Tolias et al., "Critical Appraisal of Neuroprotection Trials in Head Injury: What Have We Learned?," *NeuroRx®*, vol. 1, pp. 71-79, 2004.

Tse et al., "Cerebral protection in traumatic brain injury," *Surgical Practice*, vol. 9, pp. 122-125, 2005.

Maas et al., "Prognosis and Clinical Trial Desin in Traumatic Brain Injury: The IMPACT Study," *J. Neurotrauma*, vol. 24, No. 2, pp. 232-238, 2007.

Stein et al., "Does Progesterone Have Neuroprotective Properties?," *Annals of Emergency Medicine*, pp. 1-9, 2007.

Povlishock et al., "Workshop on Animal Models of Traumatic Brain Injury," *J. Neurotrauma*, vol. 11, No. 6, pp. 723-732, 1994.

Laurer et al., "Experimental models of brain trauma," *European J. Head Trauma*, vol. 3, pp. 95-110, 2000.

Finnie, "Animal models of traumatic brain injury: a review," *Aust. Vet. J.*, pp. 628-633, 2001.

Leker et al., "Experimental Models of Head Trauma," *Acta Neurochir.*, vol. 83, pp. 49-54, 2002.

Allolio et al., "High-Dose Progesterone Infusion in Healthy Males: Evidence Against Antiglucocorticord Activity of Progesterone," *European J. Endocrin.*, vol. 133, pp. 696-700, 1995.

Bender et al., Effect of Benzodiazepines and Neurosteroids on Ammonia-Induced Swelling in Cultured Astrocytes, *J. Neurosci. Res.*, vol. 54, pp. 673-680, 1998.

Canonaco et al., "Steroid Hormones and Receptors of the $GABA_A$ Supromolecular Complex," *Neuroendocrinology*, vol. 57, pp. 974-984, 1993.

Celotti et al., "The 5α-Reductase in the Brain: Molecular Aspects and Relation to Brain Function," *Frontiers in Neuroendocrinology*, vol. 13, No. 2, pp. 163-215, 1992.

Cervantes et al., "Brain Injury Following Cardiorespiratory Arrest in Cats, Effects of Alphaxolone-Alphadolone," *Bol. Estud. Med. Biol.*, vol. 37, pp. 17-27, 1989.

Chen et al., "Neuroprotective Effects of Progesterone After Transient Middle Cerebral Artery Occlusion," *J. Neurol. Sci.*, vol. 171, pp. 24-30, 1999.

Djebaili et al., "Allopregnanolone and Progesterone Decrease Cell Death and Cognitive Deficits After a Contusion of the Rat Pre-Frontal Cortex," *Neuroscience*, vol. 123, pp. 349-359, 2004.

Djebaili et al., "The Neurosteroids Progesterone and Allopregnanolone Reduce Cell Death, Gliosis, and Functional Deficits After Traumatic Brain Injury in Rats," *J. Neurotrauma*, vol. 2, pp. 106-118, 2005.

Fleming et al., "Megestrol Acetate Reverses Multidrug Resistance and Interacts with P-glycoprotein," *Cancer Chemother. Pharmacol.*, vol. 29, pp. 445-449, 1992.

Gee, "Steroid Modulation of the GABA/Benzodiazepine Receptor-Linked Chloride Ionophore," *Molecular Neurobiology*, vol. 2, pp. 291-317, 1998.

Ghezzi et al., "Neurosteroid Levels are Increased in vivo after LPS Treatment and Negatively Regulater LPS-induced TNF Productions," *European Cytokine Network*, 2000, vol. 11, No. 3, pp. 464-469.

Grossman et al., "Effects of Progesterone on the Inflammatory Response to Brain Injury in the Rat," *Brain Res.*, vol. 1008, pp. 29-39, 2004.

Hawkinson et al., "Substituted 3β-Phenylethynyl Derivative of 3α-Hydroxy-5α-pregnan-20-one: Remarkably Potent Neuroactive Steroid Modulators of γ-Aminobutyric Acid Receptors," *J. Pharmacology and Experimental Therapies*, vol. 287, No. 1, pp. 198-207, 1998.

He et al., "Alopregnanolone Facilitates Spatial Learning After Traumatic Brain Injury," *Soc. Neurosci. Abstr.*, vol. 26, p. 2296, 2000.

Hoffman et al., "Alopregnanolone Reduces Edema After Controlled Cortical Impact Injury in Rats," *Soc. Neurosci. Abstr.*, vol. 26, p. 967, 2000.

Jiang et al., "Progesterone is Neuroprotective after Transient Middle Cerebral Artery Occulusion in Male Rats," *Brain Research*, vol. 735, pp. 101-107, 1996.

Lambert et al., "Neurosteroid Modulatin of Native and Recombinant $GABA_A$ Receptors," *Cellular and Molecular Neurobiology*, vol. 16, No. 2, pp. 155-174, 1996.

Limmroth et al., "$GABA_A$-Receptor-Mediated Effects of Progesterone, Its Ring-A-Reduced Metabolites and Synthetic Neuroactive Steroids on Neurogenic Oedema in the Rat Meniges," *British Journal of Pharmacology*, vol. 117, pp. 99-104, 1996.

Maurice et al., "Neuroactive Neurosteroids as Engongenous Effectors for the Sigma1($\sigma_1$) Receptor: Pharmacological Evidence and Therapeutic Opportunities," *Jpn. J. Pharmacol.*, vol. 81, pp. 125-155, 1999.

Melcangi et al., "Steroid Metabolism and Effects in Central and Peripheral Glial Cells," *J. Neurobiol.*, vol. 40, pp. 471-483, 1999.

Michaels, "Cognitive Rehabilitation Advanced by Multifaceted Research, Conference Told," *Can. Med. Assoc. J.*, vol. 153, pp. 465-467, 1995.

Monaghan et al., "Initial Human Experience with Ganaxolone, A Neuroactive Steroid with Antiepileptic Activity," *Epilepsia*, vol. 38, No. 9, pp. 1026-1031, 1997.

Roof et al., "Progesterone Metabolites May Mediate Its Neuroprotective Effects After Traumatic Brain Injury," *J. Neurotrauma*, vol. 14, No. 12, p. 760, 1997.

Roof et al., "Gender Differences in Acute CNS Trauma and Stroke: Neuro-protective Effects of Estrogen and Progesterone," *J. Neurotrauma*, vol. 17, pp. 367-388, 2000.

Roof et al., "Progesterone Treatment Attenuates Brain Edema Following Contusion Injury in Male and Female Rats," *Restorative Neurology and Neuroscience*, vol. 4, pp. 425-427, 1992.

Roof et al., "Progesterone Facilitates Cognitive Recovery and Reduces Secondary Neuronal Loss Caused by Cortical Contusion Injury in Male Rats," *Experimental Neurology*, vol. 129, pp. 64-69, 1994.

Roof et al., "Progesterone Protects Against Lipid Peroxidation Following Traumatic Brain Injury in Rats," *Molecular and Chemical Neuropathology*, vol. 31, pp. 1-11, 1997.

Roof et al., "Progesterone Rapidly Decrease Brain Edema: Treatment Delayed up to 24 Hours is Still Effective," *Experimental Neurology*, vol. 138, pp. 246-251, 1996.

Rupprecht et al., "Steroid Receptor-Mediated Effects of Neuroactive Steroids: Characterization of Structure-Activity Relationship," *Eur. J. of Pharmacology*, vol. 303, pp. 227-234, 1996.

Ströhle et al., "Concentration of 3α-Reduced Neuroactive Steroids and Their Precursors in Plasma of Patients with Major Depression and after Clinical Recovery," *So. of Biol. Psychiatry*, vol. 45, pp. 274-277, 1999.

Taubøll et al., "The effect of Progesterone and its Metabolite 5α-pregnan-3 α-ol-20-one on Focal Epileptic Seizures in the Cat's Visual Vortex in vivo," *Epilepsy Research*, vol. 14, pp. 17-30, 1993.

Weaver et al., "Neuroprotective Activity of a New Class of Steroidal Inhibitors of the N-methyl-D-aspartate Receptor," *Proc. Natl. Acad. Sci., USA*, vol. 94, pp. 1045-=10454, 1997.

Wright et al., "Serum Progesterone Levels Correlate with Decreased Cerebral edema After Traumatic Brain Injury in Male Rats," *J. Neurotrauma*, vol. 18, pp. 901-909, 2001.

Yu et al., "Down-Regulation of the GABA Receptor Subunits mRNA levels in Mammalian Cultured Cortical Neurons Following Chronic Neurosteroid Treatment," *Molecular Brain Research*, vol. 41, pp. 163-168, 1996.

Foldvary-Schaefer et al., "Hormones and seizures," *Cleveland Clinic Journal of Medicine*, vol. 71, Supplement 2, pp. S11-S18, Feb. 2004.

Gulinello et al., "Sex differences in anxiety, sensorimotor gating and expression of the α4 subunit of the $GABA_A$ receptor in the amygdale after progesterone withdrawal," *European Journal of Neuroscience*, vol. 17, pp. 641-648, 2003.

Kulkarni et al., "Neurosteroids: A New Clas of Neuromodulators," *Drugs of Today*, vol. 31, No. 6, pp. 433-455, 1995.

Rupprecht, "Neuroactive steroids: mechanisms of action and neuropsychopharmacological properties," *Psychoneuroendocrinology*, vol. 28, pp. 139-168, 2003.

Smith, "Withdrawal properties of a neuroactive steroid: implications for $GABA_A$ receptor gene regulation in the brain and anxiety behavior," *Steroids*, vol. 67, pp. 519-528, 2002.

Rupprecht et al., "Neuroactive Steroids in Neuropsychopharmacology," *International Review of Pharmacology*, vol. 48, pp. 461-477, 2001.

Rupprecht et al., "Neuroactive steroids: molecular mechanisms of action and implications for neuropsychopharmacology," *Brain Research Reviews*, vol. 37, pp. 59-67, 2001.

Lukasiuk et al., "$GABA_A$—Mediated Toxicity of Hippocampal Neurons in Vitro," *Journal of Neurochemistry*, vol. 74, No. 6, pp. 2445-2454, 2000.

Van Den Pol et al., "Glutamate Hyperexcitability and Seizure-Like Activity Throughout the Brain and Spinal Cord Upon Relief from Chronic Glutamate Receptor Blockade in Culture," *Neuroscience*, vol. 74, No. 3, pp. 653-674, 1996.

Adams et al., "Steroid withdrawal in liver transplant recipients," *Progress in Transplantation*, vol. 11, No. 3, Sep. 2001.

Goss et al., "Behavioral effects and anatomic correlates after brain injury: a progesterone dose-response study," *Pharmacology, Biochemistry and Behavior*, vol. 76, pp. 231-242, 2003.

He et al., "Allopregnanolone, a progesterone metabolite, enhances behavioral recovery and decreases neuronal loss after traumatic brain injury," *Restorative Neurology and Neuroscience*, vol. 22, pp. 19-31, 2004.

Stein et al., "Estrogen and progesterone as neuroprotective agents in the treatment of acute brain injuries," *Pediatric Rehabilitation*, vol. 6, No. 1, pp. 13-22, 2003.

Vink et al., "Recent advances in the development of multifactorial therapies for the treatment of traumatic brain injury," *Expert Opin. Investig. Drugs*, vol. 13, No. 10, pp. 1263-1274, 2004.

Wlodarczyk et al., "Steroid withdrawal at 3 months after kidney transplantation: a comparison of two tacrolimus-based regimens," *Transplant International*, vol. 18, pp. 157-162, 2005.

Notice of Allowance issued by the Examiner on Nov. 26, 2010 in U.S. Appl. No. 12/117,217 (US 7,915,244).

Office Action issued by the Examiner on Jul. 22, 2010 in U.S. Appl. No. 12/117,217 (US 7,915,244).

Office Action issued by the Examiner on Mar. 16, 2010 in U.S. Appl. No. 12/117,217 (US 7,915,244).

Office Action issued by the Examiner on Aug. 19, 2009 in U.S. Appl. No. 12/117,217 (US 7,915,244).

Wilson et al., "Free Radicals, Antioxidants, and Neurologic Injury: Possible Relationship to Cerebral Protection by Anesthetics," Journal of Neurosurgical Anesthesiology, vol. 14, No. 1, pp. 66-79, 2002.

* cited by examiner

METHODS FOR THE TREATMENT OF A TRAUMATIC CENTRAL NERVOUS SYSTEM INJURY

CROSS-REFERENCE TO RELATED APPLICATIONS

This application is a continuation of U.S. patent application Ser. No. 12/117,217, filed May 8, 2008, which is a continuation of U.S. patent application Ser. No. 11/527,816, filed Sep. 27, 2006, is a continuation-in-part of International Patent Application No. PCT/US 2006/010797, filed Mar. 24, 2006, which claims the benefit of U.S. Provisional Application No. 60/664,728, filed Mar. 24, 2005 and U.S. Provisional Application No. 60/729,663, filed Oct. 24, 2005; each of which is hereby incorporated by reference in its entirety.

FEDERALLY SPONSORED RESEARCH OR DEVELOPMENT

This invention was made with United States Government support under 1R01 N5 39097-01A1 awarded by the National Institute of Neurological Disorders and Stroke (HINDS), National Institutes of Health. The United States Government has certain rights in the invention.

FIELD OF THE INVENTION

The invention relates to methods for treating a traumatic injury to the central nervous system.

BACKGROUND OF THE INVENTION

Between 1.5 and 2 million Americans sustain a traumatic brain injury (TBI) each year (Anonymous, "Traumatic Brain Injury," *Center for Disease Control and Prevention, National Center for Injury Prevention and Control*, 2003, Vol. 2003). In the U.S. it is estimated that TBI is responsible for 50,000 deaths and 100,000 hospitalizations annually (Anonymous, "Traumatic Brain Injury," *Center for Disease Control and Prevention, National Center for Injury Prevention and Control*, 2003, Vol. 2003). Over 80,000 are disabled annually, approximately 17,000 of whom require specialized care for life (Kraus (1997) "Epidemiology of Head Injury," in *Head Injury*, ed. Cooper (Williams & Wilkins Co., Baltimore) pp 1-19; Selecki et al. (1982) *Australian & New Zealand Journal of Surgery* 52(1):93-102). In addition to the initial lesion created by abrupt trauma to the brain, excessive biomechanical force initiates a cascade of secondary deleterious events that can dramatically increase lesion size, morbidity, and mortality for days to months after the initial injury (McIntosh et al. (1996) *Lab Invest*, 74(2):315-42; Stambrook et al. (1990) *Can J Surg* 33(2):115-8). Despite the enoimity of the problem, an effective pharmacological treatment for TBI in humans has not been identified.

Continuous intravenous (IV) infusion allows rapid drug delivery and achievement of a continuous steady state serum concentration, but this route for administration of progesterone is not FDA approved in the United States. Only three human studies involving the use of IV progesterone in the US have been reported. In an FDA-approved (IND 33,580) phase I clinical trial, Christen, et al. administered IV progesterone dissolved in an ethanol-Intralipid 20% fat emulsion combined with doxorubicin over 24 hours to 32 cancer patients without toxic effects (Christen et al. (1993) *Journal of Clinical Oncology* 11(12):2417-2426). In a second study, Allolio et al. reported that steady state serum concentrations ($C_{SS}$) of progesterone could be achieved in healthy male volunteers (Allolio et al. (1995) *European Journal of Endocrinology* 133(6):696-700). The third study was modeled after the study performed by Christen et al, but was a phase II trial testing the effect of coadministration of high-dose progesterone on the pharmacokinetics of paclitaxel. The manuscript did not present detailed information on the pharmacokinetics of progesterone.

Following a traumatic injury to the central nervous system, a cascade of physiological events leads to neuronal loss including, for example, an inflammatory immune response and excitotoxicity resulting from the initial impact disrupting the glutamate, acetylcholine, cholinergic, $GABA_A$, and NMDA receptor systems. In addition, the traumatic CNS injury is frequently followed by brain and/or spinal cord edema that enhances the cascade of injury and leads to further secondary cell death and increased patient mortality. Methods are needed for the in vivo treatment of traumatic CNS injuries that are successful at providing subsequent trophic support to remaining central nervous system tissue, and thus enhancing functional repair and recovery, under the complex physiological cascade of events which follow the initial insult.

SUMMARY OF THE INVENTION

Methods of treating a subject with a traumatic central nervous system injury, more particularly, a traumatic brain injury, are provided. The methods comprise treatment of a traumatic brain injury in a human subject by administering to the subject in need thereof a therapeutically effective concentration of progesterone or synthetic progestin. In specific methods, treatment of a traumatic brain injury in a human subject comprises a therapy comprising a constant or a two-level dosing regime of progesterone or synthetic progestin. In further methods, the constant or two-level dosing regime of progesterone or synthetic progestin results in a serum progesterone or synthetic progestin level of about 100 ng/ml to about 1000 ng/ml. In other methods, the constant or two-level dosing regime results in a serum progesterone or synthetic progestin level of less than 450 ng/ml.

Further provided is a method of treating a traumatic brain injury in a human subject. The method comprises administering to the subject in need thereof at least one cycle of therapy, wherein the cycle of therapy comprises administering a therapeutically effective two-level intravenous dosing regime of progesterone or synthetic progestin. The two-level dosing regime can comprise a first time period, wherein a higher hourly dose of progesterone or synthetic progestin is administered to the subject, followed by a second time period, wherein a lower hourly dose of progesterone or synthetic progestin is administered to the subject. In specific methods, the first time period comprises an hourly dose of progesterone or synthetic progestin of about 0.1 mg/kg to about 7 mg/kg. In other methods, the second time period comprises an hourly dose of progesterone or synthetic progestin of about 0.05 mg/kg to about 5 mg/kg. In other methods, a third time period comprising a tapered administration protocol is added to the progesterone or synthetic progestin dosing regime.

DETAILED DESCRIPTION OF THE INVENTION

Figure 1:
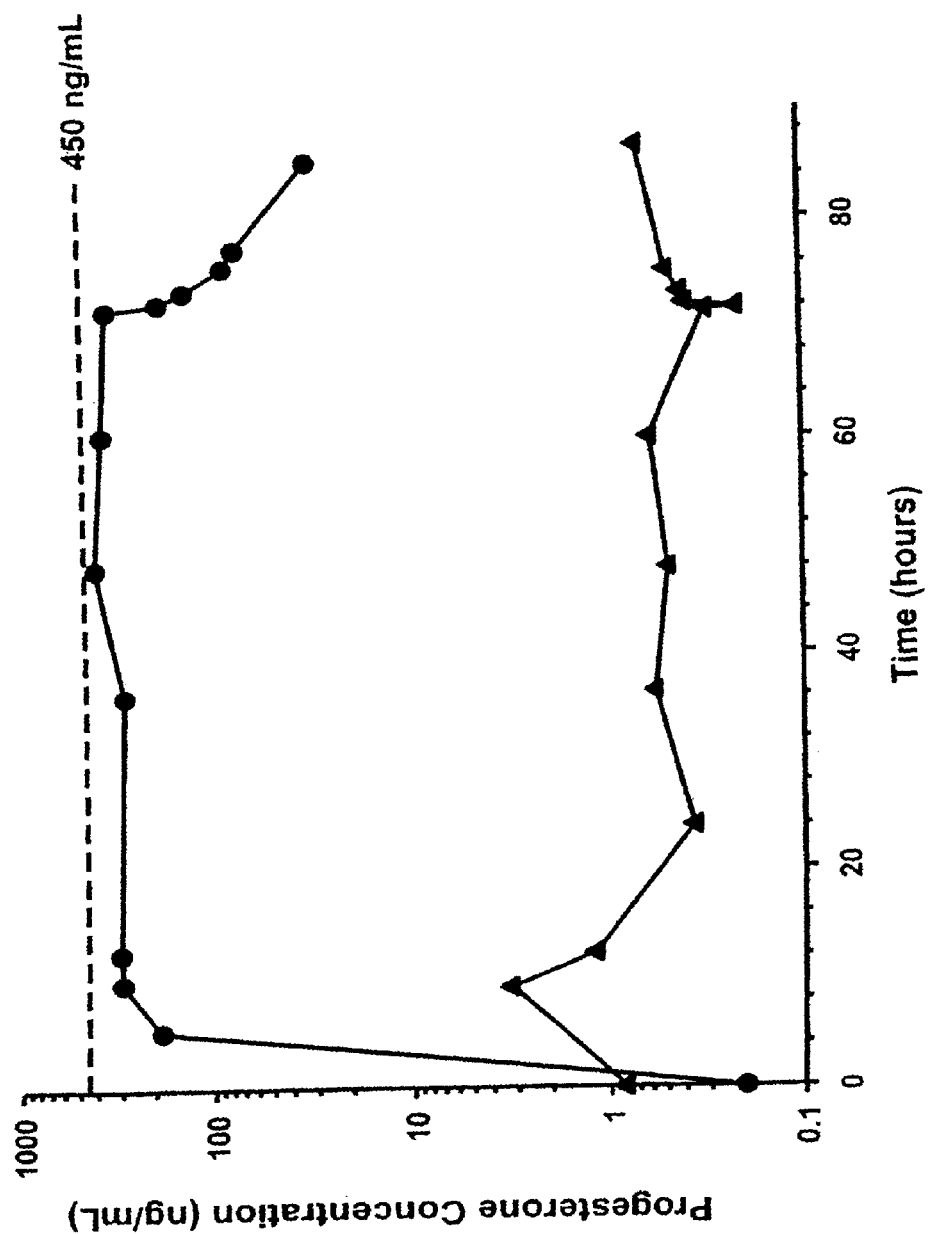
FIG. 1 shows stable progesterone concentrations can be achieved rapidly using continuous intravenous infusion. The closed circles represent the serum concentration-time profile for one patient receiving progesterone. The solid triangles represent the serum concentration-time profile for a patient receiving a placebo infusion. Progesterone concentrations for patients receiving a placebo infusion remained constant throughout the study period. $C_{SS}$ concentrations in patients receiving progesterone are rapidly reached and, once achieved, are stable throughout the infusion period.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to methods of treating a human subject with a traumatic central nervous system injury, more particularly, a traumatic brain injury. The methods comprise treatment of a traumatic brain injury in a human subject by administering to the subject in need thereof a therapeutically effective concentration of progesterone or synthetic progestin. As discussed in more detail below, the methods for treating a traumatic brain injury in a human subject comprise a therapy comprising a dosing regime of progesterone or synthetic progestin.

A traumatic injury to the CNS is characterized by a physical impact to the central nervous system. For example, a traumatic brain injury results when the brain is subjected to a physical force that results in progressive neuronal cell damage and/or cell death. A traumatic brain injury may result from a blow to the head and manifest as either an open or closed injury. Severe brain damage can occur from lacerations, skull fractures, and conversely, even in the absence of external signs of head injury. Accordingly, the methods of the invention can be used to treat a traumatic brain injury, including, blunt traumas, as well as, penetrating traumas.

The physical forces resulting in a traumatic brain injury may cause their effects by inducing three types of injury: skull fracture, parenchymal injury, and vascular injury. Parenchymal injuries include concussion, direct parenchymal injury and diffuse axonal injury. Concussions are characterized as a clinical syndrome of alteration of consciousness secondary to head injury typically resulting from a change in the momentum of the head (movement of the head arrested against a ridged surface). The pathogenesis of sudden disruption of nervous activity is unknown, but the biochemical and physiological abnormalities that occur include, for example, depolarization due to excitatory amino acid-mediated ionic fluxes across cell membranes, depletion of mitochondrial adenosine triphosphate, and alteration in vascular permeability. Post-concussive syndrome may show evidence of direct parenchymal injury, but in some cases there is no evidence of damage.

Contusion and lacerations are conditions in which direct parenchymal injury of the brain has occurred, either through transmission of kinetic energy to the brain and bruising analogous to what is seen in soft tissue (contusion) or by penetration of an object and tearing of tissue (laceration). A blow to the surface of the brain leads to rapid tissue displacement, disruption of vascular channels, and subsequent hemorrhage, tissue injury and edema. Morphological evidence of injury in the neuronal cell body includes pyknosis of nucleus, eosinophilia of the cytoplasm, and disintegration of the cell. Furthermore, axonal swelling can develop in the vicinity of damage neurons and also at great distances away from the site of impact. The inflammatory response to the injured tissue follows its usual course with neutrophiles preceding the appearance of macrophages.

In accordance with the methods of the present invention, progesterone or synthetic progestin is used to promote a positive therapeutic response with respect to the traumatic central nervous system injury. By "treatment" is intended any improvement in the subject having the traumatic CNS injury including both improved morphological recovery (i.e., enhanced tissue viability) and/or behavioral recovery. The improvement can be characterized as an increase in either the rate and/or the extent of behavioral and anatomical recovery following the traumatic CNS injury. Accordingly, a "positive therapeutic response" includes both a complete response and a partial response. Various methods to determine if a complete or a partial therapeutic response has occurred are discussed in detail elsewhere herein.

Neurodegeneration is the progressive loss of neurons in the central nervous system. As used herein, "neuroprotection" is the arrest and/or reverse progression of neurodegeneration following a traumatic central nervous system injury. Multiple physiological events lead to the neurodegeneration of the CNS tissues following a traumatic CNS injury. These events include, for example, cerebral edema, destruction of vascular integrity, increase in the immune and inflammatory response, demyelinization, and lipid peroxidation. Hence, the methods of the invention also find use in reducing and/or preventing the physiological events leading to neurodegeneration. Specifically, the present invention provides methods for reducing or eliminating neuronal cell death, edema, ischemia, and enhancing tissue viability following a traumatic injury to the central nervous system.

The progesterone or synthetic progestin therapy of the invention is administered to a subject having a traumatic CNS injury. As defined herein, the subject can be any mammal, preferably a human. In specific embodiments, the human is an adult (over 18 years of age), while in other embodiments, the human is a child (under 18 years of age). The child can be a neonate, infant, toddler, pre-pubescent or post-pubescent and range in age from about birth, 1 month to about 2 year, about 1 year to about 5 years, about 4 years to about 9 years, about 8 years to about 14, or about 13 to about 18 years of age. In addition, the human can be about 55 to 60, 60 to 65, 65 to 70, 70 to 75, 75 to 80, 80 to 85, 85 to 90, 90 to 95 or older.

The present invention provides a method of treating a traumatic CNS injury by administering to a subject progesterone or synthetic progestin in a therapeutically effective amount. By "therapeutically effective amount" is meant the concentration of a progesterone or synthetic progestin that is sufficient to elicit a therapeutic effect. Thus, the concentration of a progesterone or synthetic progestin in an administered dose unit in accordance with the present invention is effective in the treatment or prevention of neuronal damage that follows a traumatic injury to the CNS and hence, elicits a neuroprotective effect. The therapeutically effective amount will depend on many factors including, for example, the specific activity of the progesterone or synthetic progestin, the severity and pattern of the traumatic injury, the resulting neuronal damage, the responsiveness of the patient, the weight of the patient, along with other intraperson variability, the method of administration, and the progesterone or synthetic progestin formulation used.

The compositions comprising the therapeutically effective concentration of progesterone or synthetic progestin may be administered using any acceptable method known in the art. Thus, for example, the pharmaceutical composition comprising progesterone or synthetic progestin can be administered by any method, including intravenous (IV) injection, intramuscular (IM) injection, subcutaneous (SC) injection, or vaginal administration. In specific embodiments of the invention, the pharmaceutical composition comprising progesterone or synthetic progestin is administered by IV injection. When administered intravenously, the pharmaceutical composition comprising the progesterone or synthetic progestin can be administered by infusion over a period of about 1 to about 120 hours. In some embodiments, infusion of the progesterone or synthetic progestin occurs over a period of about 24 to about 72 hours, over a period of about 48 to about 96 hours, or over a period of about 24 to about 120 hours.

In one embodiment of the present invention, progesterone or synthetic progestin is administered via parenteral (including intraperitoneal, intravenous, subcutaneous, or intramuscular) administration in a dose of about 0.1 ng to about 100 g per kg of body weight, about 10 ng to about 50 g per kg of body weight, from about 100 ng to about 1 g per kg of body weight, from about 1 µg to about 100 mg per kg of body weight, from about 1 µg to about 50 mg per kg of body weight, from about 0.01 mg to about 10 mg per kg of body weight, from about 0.05 mg to about 5 mg per kg of body weight, from about 0.1 mg to about 1 mg per kg of body weight, from about 0.1 mg to about 0.5 mg per kg of body weight, from about 0.5 mg to about 1 mg per kg of body weight, from about 0.5 mg to about 0.7 mg per kg of body weight, from about 0.7 mg to about 1 mg per kg of body weight, from about 0.1 mg to about 7 mg per kg of body weight, from about 0.1 mg to about 7.1 mg per kg of body weight, from about 0.4 to about 0.6 mg/kg, from about 0.45 to about 0.55 mg/kg, about 0.5 mg/kg, from about 0.6 to about 0.8 mg/kg, from about 0.65 to about 0.75 mg/kg, about 0.7 mg/kg, from about 1 mg to about 500 mg per kg of body weight; and from about 1 mg to about 50 mg per kg of body weight. Alternatively, the amount of progesterone or synthetic progestin administered to achieve a therapeutic effective dose is about or at least about 0.1 ng, 1 ng, 10 ng, 100 ng, 1 µg, 10 µg, 100 µg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In one embodiment of the present invention, progesterone or synthetic progestin is administered via a constant dosing regimen in a dose of about 0.01 to about 10 mg/kg/h, from about 0.05 to about 5 mg/kg/h, from about 0.1 to about 1 mg/kg/h, from about 0.4 to about 0.6 mg/kg/h, from about 0.45 to about 0.55 mg/kg/h, about 0.5 mg/kg/h, from about 0.6 to about 0.8 mg/kg/h, from about 0.65 to about 0.75 mg/kg/h, or about 0.7 mg/kg/h. Alternatively, the amount of progesterone or synthetic progestin administered to achieve a therapeutic effective dose is about or at least about 0.1 ng, 1 ng, 10 ng, 100 ng, 1 µg, 10 µg, 100 µg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight per hour or greater.

Progesterone or synthetic progestin may be administered once or several times a day. The duration of the treatment may be once per day for a period of about 1, 2, 3, 4, 5, 6, 7 days or more. The daily dose can be administered either by a single dose in the form of an individual dosage unit or several smaller dosage units or by multiple administration of subdivided dosages at certain intervals.

For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the subject from the secondary wave of edema that may occur over the first several days post-injury.

In specific embodiments of the invention, the subject undergoing the therapy with progesterone or synthetic progestin is administered a constant progesterone or synthetic progestin dosing regimen. By "constant progesterone or synthetic progestin dosing regimen" is intended the subject undergoing therapy with progesterone or synthetic progestin is administered a constant total hourly infusion dose of progesterone or synthetic progestin over the course of treatment. This hourly dose of progesterone or synthetic progestin is partitioned into a series of equivalent doses that are administered according to an appropriate dosing schedule depending on the method of administration. The duration of the constant progesterone or synthetic progestin dosing regimen is about 12, 24, 36, 60, 72, 84, or 120 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours.

In other embodiments of the invention, the therapy with the progesterone or synthetic progestin comprises a "two-level progesterone or synthetic progestin dosing regimen." By "two-level progesterone or synthetic progestin dosing regimen" is intended the subject undergoing the therapy with progesterone or synthetic progestin is administered progesterone or synthetic progestin during two time periods of progesterone or synthetic progestin dosing. The two-time periods can have a combined duration of about 12 hours to about 7 days, including, 1, 2, 3, 4, or 5 days or about 15, 15, 30, 35, 40, 45, 50, 55, 60, 65, 70, 75, 80, 85, 90, 95, 100, 105, 110, 115, 120, 125, 130, 135, 140, or 144 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours. In one embodiment, the two-level progesterone or synthetic progestin dosing regimen has a combined duration of about 1 day to about 5 days; in other embodiments, the two-level progesterone or synthetic progestin dosing regimen has a combined duration of about 1 day to about 3 days.

In one embodiment, the total hourly dose of progesterone or synthetic progestin that is to be administered during the first and second time periods of the two-level progesterone or synthetic progestin dosing regimen is chosen such that a higher total infusion dose of progesterone or synthetic progestin per hour is given during the first time period and a lower infusion dose of progesterone or synthetic progestin per hour is given during the second time period. The duration of the individual first and second time periods of the two-level progesterone or synthetic progestin dosing regimen can vary, depending upon the health of the individual and history of the traumatic injury. Generally, the subject is administered higher total infusion dose of progesterone or synthetic progestin per hour for at least 1, 2, 3, 4, 5, 6, 12 or 24 hours out of the 1 day to 5 day two-level progesterone or synthetic progestin dosing regimen. The length of the second time period can be adjusted accordingly, and range for example, from about 12 hrs, 24 hrs, 36 hrs, 48 hrs, 60 hrs, 72 hrs, 84 hrs, 96 hrs, 108 hrs, 120 hrs or about 12 to about 36 hrs, about 24 to about 36 hrs, about 24 to about 48 hrs, about 36 hrs to about 60 hours, about 48 hrs to about 72 hrs, about 60 hrs to about 84 hours, about 72 hrs to about 96 hrs, or about 108 hrs to about 120 hrs. Thus, for example, where the two-level progesterone or synthetic progestin dosing regimen has a combined duration of 3 days, the higher total doses of progesterone or synthetic progestin could be administered for the first hour, and the lower total hourly dose of progesterone or synthetic progestin could be administered for hours 2 to 72.

Though specific dosing regimens are disclosed herein below, it is recognized that the invention encompasses any administration protocol that provides for a two-level progesterone or synthetic progestin dosing regimen that provides for initial exposure to higher hourly doses of progesterone or synthetic progestin, and subsequent exposure to a lower hourly doses of progesterone or synthetic progestin. For example, the first progesterone or synthetic progestin dosing regime can be administered by a single bolus injection, followed by a second time period of progesterone or synthetic progestin IV administration.

In still further embodiments, the total infusion dose of progestrone per hour that is to be administered during the first and second time periods of the two-level progesterone or synthetic progestin dosing regimen is chosen such that a lower total hourly dose of progesterone or synthetic progestin is given during the first time period and a higher hourly dose of progesterone or synthetic progestin is given during the second time period.

Area under the curve (AUC) refers to the area under the curve that tracks the serum concentration (nmol/L) of progesterone or synthetic progestin over a give time following the IV administration of the reference progesterone or synthetic progestin standard. By "reference progesterone or synthetic progestin standard" is intended the formulation of progesterone or synthetic progestin that serves as the basis for determination of the total hourly progesterone or synthetic progestin dose to be administered to a human subject with a traumatic central nervous system injury in accordance with the desired constant or two-level progesterone or synthetic progestin dosing regimen to achieve the desired positive effect, i.e., a positive therapeutic response that is improved with respect to that observed without administration of progesterone or synthetic progestin. For the determination of the AUC for the reference progesterone or synthetic progestin standard, see the Experimental Section, Example 1. Accordingly, the total hourly dose of progesterone or synthetic progestin to be administered during the constant or two-level progesterone or synthetic progestin dosing regimen can therefore allow for a final serum level of progesterone or synthetic progestin of about 100 ng/ml to about 2000 ng/ml, about 100 ng/ml to about 1000 ng/ml, about 1100 ng/ml to about 1450 ng/ml, about 100 ng/ml to about 250 ng/ml, about 100 ng/ml to about 275 ng/ml, about 100 ng/ml to about 300 ng/ml, about 100 ng/ml to about 325 ng/ml, about 100 ng/ml to about 350 ng/ml, about 100 ng/ml to about 375 ng/ml, about 100 ng/ml to about 400 ng/ml, about 100 ng/ml to about 425 ng/ml, about 100 ng/ml to about 450 ng/ml, about 125 ng/ml to about 250 ng/ml, about 125 ng/ml to about 275 ng/ml, about 125 ng/ml to about 300 ng/ml, about 125 ng/ml to about 325 ng/ml, about 125 ng/ml to about 350 ng/ml, about 125 ng/ml to about 375 ng/ml, about 125 ng/ml to about 400 ng/ml, about 125 ng/ml to about 425 ng/ml, about 125 ng/ml to about 450 ng/ml, about 150 ng/ml to about 250 ng/ml, about 150 ng/ml to about 275 ng/ml, about 150 ng/ml to about 300 ng/ml, about 150 ng/ml to about 325 ng/ml, about 150 ng/ml to about 350 ng/ml, about 150 ng/ml to about 375 ng/ml, about 150 ng/ml to about 400 ng/ml, about 150 ng/ml to about 425 ng/ml, about 150 ng/ml to about 450 ng/ml, about 175 ng/ml to about 250 ng/ml, about 175 ng/ml to about 275 ng/ml, about 175 ng/ml to about 300 ng/ml, about 175 ng/ml to about 325 ng/ml, about 175 ng/ml to about 350 ng/ml, about 175 ng/ml to about 375 ng/ml, about 175 ng/ml to about 400 ng/ml, about 175 ng/ml to about 425 ng/ml, about 175 ng/ml to about 450 ng/ml, about 200 ng/ml to about 300 ng/ml, about 200 ng/ml to about 325 ng/ml, about 200 ng/ml to about 350 ng/ml, about 200 ng/ml to about 375 ng/ml, about 200 ng/ml to about 400 ng/ml, about 200 ng/ml to about 425 ng/ml, about 200 ng/ml to about 450 ng/ml, about 200 ng/ml to about 500 ng/ml, about 200 ng/ml to about 550 ng/ml, about 300 ng/ml to about 400 ng/ml, about 300 ng/ml to about 450 ng/ml, about 300 ng/ml to about 500 ng/ml, about 300 ng/ml to about 550 ng/ml, about 350 ng/ml to about 450 ng/ml, about 350 ng/ml to about 500 ng/ml, about 350 ng/ml to about 550 ng/ml, about 400 ng/ml to about 550 ng/ml, about 500 ng/ml to about 650 ng/ml, about 600 ng/ml to about 750 ng/ml, about 700 ng/ml to about 850 ng/ml, about 800 ng/ml to about 950 ng/ml, about 900 ng/ml to about 1050 ng/ml, about 1000 ng/ml to about 1150 ng/ml, about 1100 ng/ml to about 1250 ng/ml, about 1200 ng/ml to about 1350 ng/ml, about 1300 ng/ml to about 1500 ng/m, about 1400 ng/ml to about 1600 ng/m, about 1500 ng/ml to about 1700 ng/m, about 1600 ng/ml to about 1800 ng/m, about 1700 ng/ml to about 1900 ng/m, or about 1800 ng/ml to about 2000 ng/m.

In specific embodiments, the serum level of progesterone or synthetic progestin comprises about 100 ng/ml, 125 ng/ml, 150 ng/ml, 175 ng/ml, 200 ng/ml, 210 ng/ml, 220 ng/ml, 230 ng/ml, 240 ng/ml, 250 ng/ml, 260 ng/ml, 270 ng/ml, 280 ng/ml, 290 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 625 ng/ml, 650 ng/ml, 675 ng/ml, 700 ng/ml, 725 ng/ml, 750 ng/ml, 775 ng/ml, 800 ng/ml, 825 ng/ml, 850 ng/ml, 875 ng/ml, 900 ng/ml, 925 ng/ml, 950 ng/ml, 975 ng/ml, 1000 ng/ml, 1100 ng/ml, 1200 ng/ml, 1300 ng/ml, 1400 ng/ml, 1500 ng/ml, 1600 ng/ml, 1700 ng/ml, 1800 ng/ml, 1900 ng/ml, or 2000 ng/ml.

In other embodiments, the serum level of progesterone or synthetic progestin comprises less than 200 ng/ml, 225 ng/ml, 250 ng/ml, 275 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 625 ng/ml, 650 ng/ml, 675 ng/ml, 700 ng/ml, 725 ng/ml, 750 ng/ml, 775 ng/ml, 800 ng/ml, 825 ng/ml, 850 ng/ml, 875 ng/ml, 900 ng/ml, 925 ng/ml, 950 ng/ml, 975 ng/ml, or 1000 ng/ml.

In other embodiments, the serum level of progesterone or synthetic progestin comprises at least 100 ng/ml, 125 ng/ml, 150 ng/ml, 175 ng/ml, 200 ng/ml, 225 ng/ml, 250 ng/ml, 275 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 625 ng/ml, 650 ng/ml, 675 ng/ml, 700 ng/ml, 725 ng/ml, 750 ng/ml, 775 ng/ml, 800 ng/ml, 825 ng/ml, 850 ng/ml, 875 ng/ml, 900 ng/ml, 925 ng/ml, 950 ng/ml, or 975 ng/ml.

While not being bound by any mechanism of action, the pharmacokinetics of progesterone in patients with traumatic brain injury are significantly different than the pharmacokinetics observed in patients without traumatic brain injury. Differences include a higher clearance, longer half life and higher volume of distribution, which result in lower than expected serum levels of progesterone. Thus, in one embodiment of the present invention, administration of progesterone or synthetic progestin to subjects in need of therapy (e.g., patients with traumatic brain injury) results in a final serum level of progesterone or synthetic progestin that is significantly lower than the serum level achieved in healthy subjects (e.g., subjects without traumatic brain injury) administered the same dose of progesterone or synthetic progestin. In one embodiment, the serum level of progesterone or synthetic progestin after administration to a subject in need of therapy is at least about 10 to about 300 ng/ml lower than the serum level achieved in healthy subjects, e g., at least about 25, 50, 75, 100, 125, 150, 175, 200, 225, 250, 275, or 300 ng/ml lower. In a further embodiment, the lower serum level of progesterone or synthetic progestin is due at least in part to a lower clearance rate in subjects in need of therapy as compared to healthy subjects.

The methods of the present invention also contemplate embodiments where a subject undergoing a constant progesterone or synthetic progestin therapy or a two-level progesterone or synthetic progestin dosing regimen is given a time period off from progesterone or synthetic progestin dosing. For example, when a progesterone or synthetic progestin dosing regime is performed, the time period off from progesterone or synthetic progestin can occur between the conclusion of the first time period of the two-level progesterone or synthetic progestin dosing regimen and the initiation of the second time period of the two-level progesterone or synthetic progestin dosing regimen. For example, one could contemplate the first time period being administered in a pre-hospital setting, for instance at the site of the trauma. The second time period could then begin upon arrival at a hospital. In these embodiments, the two-level progesterone or synthetic progestin dosing regimen is interrupted such that progesterone or synthetic progestin dosing is withheld for a period of about 15 minutes, 30 minutes, 1 hr, 2 hr, 3 hr, 4 hr, 5 hr, 6 hr or more.

In other embodiments, the constant progesterone or synthetic progestin therapy or the two-level progesterone or synthetic progestin therapy comprises a final time period in which the administration of progesterone or synthetic progestin is tapered. By "tapered administration" is meant an administration protocol which reduces the dose of administration to the patient and thereby produces a gradual reduction and eventual elimination of progesterone or synthetic progestin, either over a fixed period of time or a time determined empirically by a physician's assessment based on regular monitoring of a therapeutic response of a subject to a traumatic CNS injury. The period of the tapered progesterone or synthetic progestin administration can be about 12, 24, 36, 48 hours or longer. Alternatively, the period of the tapered progesterone or synthetic progestin administration can range from about 1 to 12 hours, about 12 to about 48 hours, or about 24 to about 36 hours.

The drug taper employed could be a "linear" taper. For example, a "10%" linear taper from 500 mg would go 500, 450, 400, 350, 300, 250, 200, 150, 100, 50. Alternatively, an exponential taper could be employed which, if the program outlined above is used as an example, the exponential taper would be, e.g., 500, 450, 405, 365, 329, 296, 266, 239, etc. Accordingly, about a 5%, 10%, 20%, 30%, or 40% linear or exponential taper could be employed in the methods of the invention. In addition, a linear or exponential taper of about 1% to 5%, about 6% to 10%, about 11% to 15%, about 16% to 20%, about 21% to 25%, about 26% to 30%, about 31% to 35%, about 36% to 40% could be employed. Alternatively, the taper schedule can be determined based on the physician's assessment of the patient's response to therapy. Additional methods of tapered administration can be found, for example, in U.S. Provisional Application 60/729,663, filed Oct. 24, 2005, herein incorporated by reference in its entirety.

Where a subject undergoing therapy in accordance with the previously mentioned dosing regimens exhibits a partial response, or a relapse following completion of the first cycle of the therapy, subsequent courses of progesterone or synthetic progestin therapy may be needed to achieve a partial or complete therapeutic response. Thus, subsequent to a period of time off from a first treatment period, which may have comprised a constant progesterone or synthetic progestin dosing regimen or a two-level progesterone or synthetic progestin dosing regimen, a subject may receive one or more additional treatment periods comprising either constant or two-level progesterone or synthetic progestin dosing regimens. Such a period of time off between treatment periods is referred to herein as a time period of discontinuance. It is recognized that the length of the time period of discontinuance is dependent upon the degree of subject response (i.e., complete versus partial) achieved with any prior treatment periods of the progesterone or synthetic progestin therapy.

These multiple treatment sessions are referred to herein as maintenance cycles, where each maintenance cycle comprises a completed constant or two-level progesterone or synthetic progestin dosing regimen. By "completed two-level progesterone or synthetic progestin dosing regimen" is intended the subject has been administered both the first period and the second period of progesterone or synthetic progestin dosing. The necessity for multiple maintenance cycles can be assessed by monitoring the physiological and behavioral improvement of the patient. The duration between maintenance cycles can be about 1 hr, 15 hr, 1 day, 2 day, 3 day, 4 day, 5 day, 6 day or other such time periods falling within the range of about 1 day to about 14 days.

The term "progesterone" as used herein refers to a member of the progestin family and comprises a 21 carbon steroid hormone. Progesterone is also known as D4-pregnene-3,20-dione; δ4-pregnene-3,20-dione; or pregn-4-ene-3,20-dione and it its structure is provided below as formula (I). The progesterone used in the methods of the invention can be naturally occurring or synthetic.

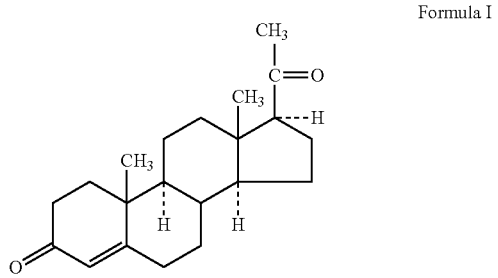

Formula I

Further encompassed by the methods of the invention are synthetic progestins. As used herein a "synthetic progestin" is a molecule whose structure is related to that of progesterone, is synthetically derived, and retains the biologically activity of progesterone (i.e., treats a traumatic CNS injury). Representative synthetic progestin include, but are not limited to, modifications that produce 17a-OH esters (i.e., 17α-hydroxyprogesterone caproate), as well as, modifications that introduce 6 α-methyl, 6-Me, 6-ene, and 6-chloro sustituents onto progesterone (i.e., medroxyprogesterone acetate, megestrol acetate, and chlomadinone acetate). Table 1 provides further, non-limiting examples, of synthetic progestins.

TABLE 1

Classification of Synthetic Progestins

| Classification by structure | Usual classification by generation* | | |
|---|---|---|---|
| | First | Second | Third |
| Estranes | Ethynodiol diacetate (with ethinyl estradiol: Demulen) Norethindrone (Micronor) Norethindrone acetate (Aygestin) | — | — |
| Gonanes | Norgestrel (Ovrette) | Levonorgestrel (Norplant; with ethinyl estradiol: Alesse, Nordette) | Desogestrel (with ethinyl estradiol: Desogen) Gestodene† Norgestimate (with ethinyl estradiol: Ortho-Cyclen, Ortho Tri-Cyclen) |
| Pregnanes | Medroxyprogesterone acetate (Provera) | — | — |

*The traditional classification is based on time since market introduction and not on structural and physiologic differences or efficacy.

The composition comprising progesterone or synthetic progestin which is employed in the methods of the invention may further comprise an inorganic or organic, solid or liquid, pharmaceutically acceptable carrier. The carrier may also contain preservatives, wetting agents, emulsifiers, solubilizing agents, stabilizing agents, buffers, solvents and salts. Compositions may be sterilized and exist as solids, particulants or powders, solutions, suspensions or emulsions. In one embodiment, the progesterone or synthetic progestin is dissolved in ethanol, or any other carrier which allows progesterone or synthetic progestin to dissolve.

The progesterone or synthetic progestin can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences* (16th ed., Osol, A. (ed.), Mack, Easton Pa. (1980)). In order to form a pharmaceutically acceptable composition suitable for effective administration, such compositions will contain an effective amount of the progesterone, either alone, or with a suitable amount of carrier vehicle.

The pharmaceutically acceptable carrier of the present invention will vary depending on the method of drug administration. The pharmaceutical carrier employed may be, for example, either a solid, liquid, or time release. Representative solid carriers are lactose, terra alba, sucorse, talc, geletin, agar, pectin, acacia, magnesium stearate, stearic acid, microcrystalin cellulose, polymer hydrogels, and the like. Typical liquid carriers include syrup, peanut oil, olive oil, cyclodextrin, intralipid, and the like emulsions. Those skilled in the art are familiar with appropriate carriers for each of the commonly utilized methods of administration. Furthermore, it is recognized that the total amount of progesterone or synthetic progestin administered as a therapeutic effective dose will depend on both the pharmaceutical composition being administered (i.e., the carrier being used) and the mode of administration.

In one embodiment, the carrier comprises cyclodextrin. For example, the formation can comprise progesterone or synthetic progestin dissolved in a 22.5% 2-hydroxypropyl-β-cyclodextrin (Sigma). See, for example, Goss et al. (2003) *Pharm. Biochem. and Behavior* 76:231-242, the contents of which is herein incorporated by reference. In yet another embodiment, the carrier comprises intralipid. In one embodiment, Intralipid® 20% (Fresenius Kabi pharmaceuticals, Clayton, N.C.) is employed. The lipophilic properties of Intralipid® 20% allow up to 4 gm of progesterone or synthetic progestin per 1 liter of intralipid to be dissolved into solution.

Administration of the progesterone or synthetic progestin may be performed by many methods known in the art. The present invention comprises all forms of dose administration including, but not limited to, systemic injection, parenteral administration, intravenous, intraperitoneal, intramuscular, transdermal, buccal, subcutaneous and intracerebroventricular administration. Alternatively, the progesterone or synthetic progestin may be administered directly into the brain or cerebrospinal fluid by any intracerebroventricular technique including, for example, lateral cerebro ventricular injection, lumbar puncture or a surgically inserted shunt into the cerebro ventricle of a patient. Methods of administering may be by dose or by control release vehicles.

Additional pharmaceutical methods may be employed to control the duration of action. Controlled release preparations may be achieved by the use of polymers to complex or absorb the progesterone or synthetic progestin. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in *Remington's Pharmaceutical Sciences* (1980).

In further embodiments of the present invention, at least one additional neuroprotective agent can be combined with the progesterone or synthetic progestin to enhance neuroprotection following a traumatic CNS injury. Such agents include, for example, compounds that reduce glutamate excitotoxicity and enhance neuronal regeneration. Such agents may be selected from, but not limited to, the group comprising growth factors. By "growth factor" is meant an extracellular polypeptide-signaling molecule that stimulates a cell to grow or proliferate. When the progesterone or synthetic progestin is administered conjointly with other pharmaceutically active agents, (i.e., other neuroprotective agents) even less of the progesterone or synthetic progestin may be therapeutically effective.

The progesterone or synthetic progestin may be administered per se or in the form of a pharmaceutically acceptable salt. When used in medicine, the salts of the progesterone or synthetic progestin should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of a progesterone or a synthetic progestin with an organic or inorganic acid, using standard methods detailed in the literature. Examples of pharmaceutically acceptable salts are organic acids salts formed from a physiologically acceptable anion, such as, tosglate, methenesulfurate, acetate, citrate, malonate, tartarate, succinate, benzoate, etc. Inorganic acid salts can be formed from, for example, hydrochloride, sulfate, nitrate, bicarbonate and carbonate salts. Also, pharmaceutically acceptable salts can be prepared as alkaline metal or alkaline earth salts, such as sodium, potassium, or calcium salts of the carboxylic acid group.

Thus the present invention also provides pharmaceutical formulations or compositions, both for veterinary and for human medical use, which comprise the progesterone or synthetic progestin or a pharmaceutically acceptable salt thereof with one or more pharmaceutically acceptable carriers thereof and optionally any other therapeutic ingredients, such as other neurotrophic agents. The carrier(s) must be pharmaceutically acceptable in the sense of being compatible with the other ingredients of the formulation and not unduly deleterious to the recipient thereof.

The compositions include those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier or both, and then, if necessary, shaping the product into desired formulations.

In one embodiment, micronize progesterone or synthetic progestin is used. The micronization process decreases particle size and enhances dissolution. Prometrian is one such example of a micronized formulation of progesterone.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing faint such as a powder or granules which are optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Further, the present invention provides liposomal folmulations of the progesterone or synthetic progestin and salts thereof. The technology for forming liposomal suspensions is well known in the art. When the progesterone or synthetic progestin or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer that forms the structure of the liposome. In either instance, the liposomes that are produced may be reduced in size, as through the use of standard sonication and homogenization techniques. The liposomal formulations containing the progesterone or synthetic progestin or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired progesterone or synthetic progestin or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts.

In addition to the aforementioned ingredients, the compositions of the invention may further include one or more accessory ingredient(s) selected from the group consisting of diluents, buffers, flavoring agents, binders, disintegrants, surface active agents, thickeners, lubricants, preservatives (including antioxidants) and the like.

Behavioral assays can be used to determine the rate and extent of behavior recovery in response to the treatment. Improved patient motor skills, spatial learning performance, cognitive function, sensory perception, speech and/or a decrease in the propensity to seizure may also be used to measure the neuroprotective effect. Such functional/behavioral tests used to assess sensorimortor and reflex function are described in, for example, Bederson et al. (1986) *Stroke* 17:472-476, DeRyck et al. (1992) *Brain Res.* 573:44-60, Markgraf et al. (1992) *Brain Res.* 575:238-246, Alexis et al. (1995) *Stroke* 26:2336-2346; all of which are herein incorporated by reference. Enhancement of neuronal survival may also be measured using the Scandinavian Stroke Scale (SSS) or the BarthI Index.

The treatment of a traumatic brain injury can be monitored by employing a variety of neurological measurements. For example, a partial therapeutic responses can be monitored by determining if, for example, there is an improvement in the subjects a) maximum daily Glasgow Coma Score; b) duration of coma; 3) daily intracranial pressure—therapeutic intensity levels; 4) extent of cerebral edema/mass effect measured on serial CT scans; and, 5) duration of ventilator support. A brief description of each of these assays is provided below.

The Glasgow Coma Score (index GCS) is a reflection of the depth of impaired consciousness and is best obtained following initial resuscitation (oxygenation, rehydration and support of blood pressure) but prior to use of sedating drugs, neuromuscular blocking agents, or endotracheal intubation.

The duration of coma will be defined as the number of hours from the time of injury that the subject is unable to purposefully respond to commands or mechanical stimulation. For non-intubated subjects, this equates to a GCS score of >8. For intubated patients, this correlates with a GCS motor score of $\geq 5$. Duration of coma has been found to be predictive of functional outcome (Uhler et al. (1994) *Neurosurgery* 34(1): 122-8; Jiang et al. (1996) *Brain Res* 735(1): 101-7; and Gonzalez-Vidal et al. (1998) *Arch Med Res* 29(2): 117-24). Time spent in a coma induced pharmacologically for reasons other than brain injury should be subtracted in the final analysis.

The intracranial pressure (ICP) of patients with severe TBI is often monitored with an intracranial pressure device. Monitoring ICP can provide a measure of cerebral edema. However, inherent variability and analysis complexities due to therapeutic interventions intended on lowering the ICP mire using ICP measurements. To adjust for these interventions a therapeutic intensity scale was developed. This scale, known as the Therapeutic Intensity Level (TIL), measures treatment aggressiveness for elevated ICPs (Allolio et al. (1995) *European Journal of Endocrinology* 133(6): 696-700; Adashi et al. (1996) *Reproductive endocrinology, surgery, and technology* Philadelphia: Lippincott-Raven; and, Beers et al. eds. (1999) *The Merck manual of diagnosis and therapy.* 17th ed., Merck Sharp & Dohme Research Laboratories,Rahway, N.J.).

The extent of cerebral edema and mass effect can be determined by CT scans. For example, the volume of focal lesions can be measured. Mass lesions, either high-density or mixed-density abnormalities, will be evaluated by measuring the area of the abnormality as a region of interest, multiplying the area by the slice thickness, and summing these volumes for contiguous slices showing the same lesion. Each lesion will be measured three times, and the mean volume will be entered. This technique has been shown to be reliable (Garcia-Estrada et al. (1993) *Brain Res* 628(1-2): 271-8).

Intracerebral lesions can be further characterized by location (frontal, temporal, parietal, occipital, basal ganglia, or any combination). When an edematous zone is present, its volume (the hypodense perimeter) can be measured and analyzed separately. Midline shift will be measured using the septum pellucidum as the midline structure. The ventricle-brain ratio (VBR) will be calculated to quantify the degree of cerebral atrophy. Levin et al. ((1981) *Archives of Neurology* 38(10):623-9) found that the VBR had satisfactory reliability across different examiners, and was related both to the severity of acute injury and neurobehavioral sequelae (Hoffman et al. (1994) *J Neurotrauma* 11(4): 417-31).

The duration of ventilator support will be defined as the number of hours the patient receives positive pressure mechanical ventilation (Uhler et al. (1994) *Neurosurgery* 34(1): 122-8; Jiang et al. (1996) *Brain Res* 735(1): 101-7; and Gonzalez-Vidal et al. (1998) *Arch Med Res* 29(2): 117-24). Time spent under ventilator support for reasons other than brain injury will be subtracted in the final analysis.

In addition to the neurological measurements discussed above, a partial therapeutic response can also be assayed through various functional and neuropsychological outcomes. Several standardized measures of neuropsychological and functional performance are known. For instance subjects may display an improvement in the Glasgow Outcome Scale (GOS)/Glasgow Outcome Scale Extender (GOSE) and/or in the Disability Rating Scale (DRS). The Glasgow Outcome Score is one of the most widely used measures of brain injury recovery in the world (Garcia-Estrada et al. (1999) *Int J Dev Neurosci* 17(2): p. 145-51). Patients are classified into one of five categories: death, persistent vegetative state, severe disability, moderate disability, and good recovery. It is easy to administer and score, and has a high degree of reliability and validity.

The Disability Rating Scale (DRS) offers more precision than the GOS for measuring outcomes of moderate brain injury (Goodman et al. (1996) *J Neurochem* 66(5): 1836-44). The DRS consists of an eight-item rating of arousal and awareness, daily living activities, physical dependence, and employability (Vedder et al. (1999) *J Neurochem* 72(6):2531-8). Inter-rater reliability for the entire DRS is high (0.97 to 0.98).

The Functional Independence Measure (FIM) can be used to assess physical and cognitive disability. It contains 18 items in the following domains: self-care, sphincter control, mobility, locomotion, communication, and social cognition (Baulieu (1997) *Mult Scler* 3(2): 105-12). The FIM has demonstrated reliability and validity as an outcome measure following moderate and severe TBI (Jung-Testas et al. (1994) *J Steroid Biochem Mol Biol* 48(1): 145-54).

The Sickness Impact Profile is one method for measuring self-perceived health status (Schumacher et al. (1995) *Ciba Found Symp* 191: p. 90-112 and Koenig et al. (1995) *Science* 268(5216):1500-3). It consists of 136 questions divided into 12 categories: sleep and rest, eating, work, home management, recreation and pastimes, ambulation, mobility, body care and movement, social interaction, alertness, behavior, emotional behavior, and communication. It has been widely used across a variety of diseases and injuries, including head injury (Thomas et al. (1999) *Spine* 24:2134-8). Baseline SIP scores will reflect pre-injury health status, while follow-up scores will examine post-injury functioning.

Having now generally described this invention, the same will be better understood by reference to certain specific examples which are included herein for purposes of illustration only, and are not intended to be limiting of the invention, unless specified.

EXPERIMENTAL

Example 1

As a first step in assessing the applicability of progesterone therapy in humans, we examined the effects of acute TBI and extracranial trauma on the pharmacokinetics of PG given by intravenous infusion. Multiple blood samples were obtained from 11 female and 21 male trauma patients receiving PG and 1 female and 3 male patients receiving placebo infusions for 72 h. Values for $C_{SS}$, CL, $t_{1/2}$ and $V_d$ were obtained using $AUC_{(0-72)}$ and post-infusion blood samples. $C_{SS}$ values were 337±135 ng/mL, which were significantly and unexpectedly lower than the target concentration of 450±100 ng/mL. The lower $C_{SS}$ is attributed to the CL, which was higher than anticipated. In addition, $t_{1/2}$ was longer and $V_d$ was higher than anticipated. There were no significant gender differences in any of these parameters. These changes are consistent with the hyperkinetic changes associated with critical injury. Our results demonstrate that stable PG concentrations can be rapidly achieved following TBI.

Methods
Patient Selection:

This study was approved by the Institutional Review Board of Emory University, the Drug Safety Monitoring Board (NINDS) and the FDA (IND #58,986). After obtaining informed consent, thirty-six patients meeting the inclusion criteria outlined as follows were studied. Treatments were randomized using a 4:1 progesterone:placebo ratio. Inclusion criteria required that each patient be ≧18 years old, have a closed head injury arising from blunt trauma, have a moderate to severe brain injury (Index Glasgow Coma Score (GCS) 4-12) and arrive in the Emergency Department and obtain informed consent (from next-of-kin) in less than 11 hours post injury. Exclusion criteria included: non-survivable injury; no neurological activity (GCS 3); mild TBI (Index GCS 13-15); unknown time of injury; severe intoxication (ETON≧250 mg %); spinal cord injury with neuro-deficits; cardiopulmonary arrest; status epilepticus on arrival; blood pressure<90 systolic—on arrival or for ≧5 minutes in duration prior to enrollment; hypoxia on arrival $pO_2$<60—on arrival or for ≧5 minutes in duration prior to enrollment; females who were pregnant; active breast or reproductive organ cancers; or known allergy to progesterone, or Intralipid® components (egg yolk or soy oil).

Drug Preparation:

Solutions of study drug were prepared by the Investigational Drug Service of Emory Healthcare as follows: Progesterone was dissolved in 95% ethanol and filtered into sterile vials using a 0.2 μ filter. Aliquots of each solution were assayed for final concentration and sterility. Stock solutions of progesterone/placebo were packaged in kits (A, B, C, D or E) that matched the randomized treatment assignments. Each kit contained six vials. Vial 1 contained 15 ml of progesterone or placebo which was used to prepare the initial bolus and first infusion dose. The remaining 5 vials contained 12 ml of progesterone or placebo for the remaining infusions. Since progesterone is soluble only in alcohol, the diluent used to compound the progesterone solution was 95% ethanol. The placebo kits were also formulated with 95% ethanol. Because of the alcohol concentration, doses of study drug were mixed with Intralipid® immediately prior to infusion. Each infusion dose was administered over 12 hours and repeated every 12 hours for a total of 72 hours. After randomizing a patient, a dosing worksheet based on body weight and final progesterone concentration was used to determine the volume of vial #1 required to be diluted in Intralipid® for a standard loading infusion rate (14 cc/hr) and the first 11 hr of the maintenance infusion (10 cc/hr). The dosing worksheet was also used to calculate the volume of study medication to be diluted in Intralipid® for each of the remaining infusion reservoirs at a standard rate of 10 cc/hr.

Stability of Progesterone Solutions.

For all stability testing, the method of Segall, et al. was used with minor modifications (Segall, et al. (1999) *Journal of Pharmaceutical & Biomedical Analysis*, 19(5):803-8). The method was originally validated to assess the stability of medroxyprogesterone acetate and estradiol valerate tablets. It is an isocratic HPLC-UV method utilizing external standardization. A 5 micron, 4.6×250 mm BDS-Hypersil C-18 column (Keystone Scientific) was used and the analyses were completed on an Agilent 1100 model HPLC system with photodiode array detector. The mobile phase consisted of 40% 0.07M ammonium acetate buffer, pH 7.2 and 60% acetonitrile. Detection was at 247 nM. A check of system suitability yielded 2769 plates per meter (minimum requirement >2500) based on the progesterone peak and a relative standard deviation (RSD) of 0.80% (minimum requirement 1.0% or less).

The tailing factor for the progesterone peak was 0.5. Reproducibility as assessed by 10 injections of the same preparation on multiple different days was always less that 10%.

For each assay, progesterone preparations were diluted 1 to 10 with ethanol and 1 µL of this dilution was injected. Under these conditions, progesterone eluted at roughly 3.5 minutes. A five point standard curve was run with each analysis.

Drug Administration:

The progesterone study drug solution was infused at the loading rate of 14 mLs/hr (0.71 mg/kg/h) for one hour, followed by a decrease in infusion rate to 10 mLs/hr (0.5 mg/kg/h) for the remaining 71 hours. Although Intralipid solutions containing progesterone were found to be stable for a minimum of 24 hours, reservoirs of study drug were prepared and changed every 12 hr during the infusion period to minimize the risk of biological contamination. Any interruptions in drug administration or other deviations from the protocol were noted on a drug administration flow sheet and taken into account when calculating the total number of mg of progesterone actually administered to each patient.

Sampling Paradigm:

Nine (5 ml) samples were obtained at the following times during the infusion: pre-infusion (0), 4, 6, 12, 24, 36, 48, 60, and 72 hours. An additional five samples were obtained following cessation of infusion at: 0.5, 1, 2, 4 and 8 hours. Samples were allowed to clot, and then centrifuged. After that, the serum was removed and stored at −70° C. until analyzed.

Serum Progesterone Analysis:

Serum progesterone concentrations were measured using the Immulite® progesterone chemi-luminescent enzyme immunoassay by the Immunology Laboratory of the Department of Pathology, Emory University Hospital. The within and between day coefficients of variation for the assay were both <10%. We confirmed the accuracy of our assay by comparing the results of 9 samples over the range 0.5 to 700 ng/mL assayed in our laboratory with those assayed by a reference laboratory (The Nichols Institute, San Juan Capistrano, Calif.).

Pharmacokinetic Analysis:

The primary pharmacokinetic parameter, CL, was estimated as the ratio of the dose to area under the serum concentration-time curve (AUC). AUC's were calculated using the linear trapezoidal rule (Veng-Pedersen (1989) *Clin Pharmacokinet*, 17(6):424-40). The elimination phase rate constant, $k_e$, was calculated from the serum concentration-time data following the termination of the infusion using iterative non-linear regression (WinNonlin®, Pharsight Corporation, Mountain View, Calif.). Volume of Distribution was estimated as the ratio of CL and $k_e$. $C_{ss}$ was estimated as the ratio of Dose and CL. Actual $C_{ss}$ was defined as the concentration achieved when the slope of the serum concentration-time curve for three or more consecutive samples was not different from zero.

Statistical Analysis:

A 't' test for repeated measures and a Spearman's rank correlation coefficient were used to compare the progesterone concentrations measured by our laboratory with those measured by the Nichols Institute. Predicted $C_{ss}$ concentrations were calculated as the ratio of the infusion rate/clearance. Differences between predicted and measured Css were made using a 't' test for repeated measures. A Bland-Altman analysis was conducted to assess the magnitude of any bias associated with this approach (Bland and Altman (1986) *Lancet*, 1(8476):307-10). Pharmacokinetic parameter comparisons between male and female were accomplished using a 't' test for independent means. A p value of less than 0.05 was considered the minimum level for rejection of the null hypothesis.

Results

Thirty-six patients were studied. Thirty-two (21 males and 11 females) received progesterone and four (3 males and 1 female) received a placebo infusion. There were no significant differences in the pre-infusion progesterone concentrations between females (2.86±1.37 ng/mL) and males (2.53±1.73 ng/mL)(p<0.5). Pre-infusion progesterone concentrations for the patients receiving placebo were 2.1±0.8 ng/mL and were not significantly different from patients who received progesterone. In addition, these pre-infusion values did not significantly change over the 84 hour time course of the study. FIG. 1 is a representative serum concentration-time profile for one patient receiving progesterone and one patient receiving a placebo infusion and in whom a complete sampling paradigm was possible. Progesterone concentrations for patients receiving a placebo infusion remained constant throughout the study period. $C_{SS}$ concentrations in patients receiving progesterone were rapidly reached and, once achieved, were stable throughout the infusion period. Complete peri- and post-infusion sampling was only possible in 7/11 females and 10/21 males because of the critical nature of the injuries sustained by the study patients. $C_{SS}$ values in the current study were lower than expected based on those reported for infusions of progesterone in cancer patients (Christen et al. (1993) *Journal of Clinical Oncology* 11(12): 2417-2426).

Figure 2:
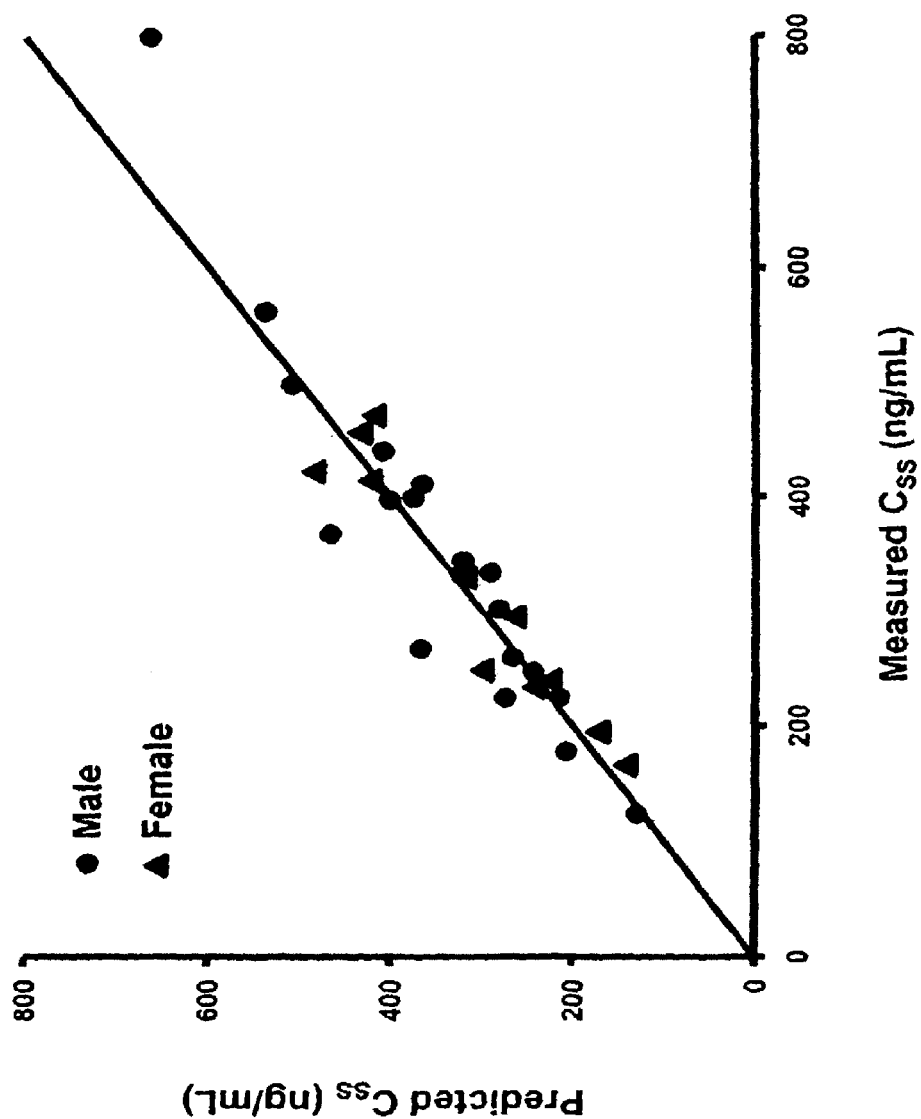
FIG. 2 shows there is a significant correlation between predicted and measured $C_{SS}$. $C_{ss}$ were predicted as the ratio of infusion rate and CL. The predicted values were compared to $C_{SS}$ measured for each patient by plotting each pair of values against the line of identity. The Spearman Rank correlation coefficient for this relationship was 0.946 ($p<0.001$).
Figure 3:
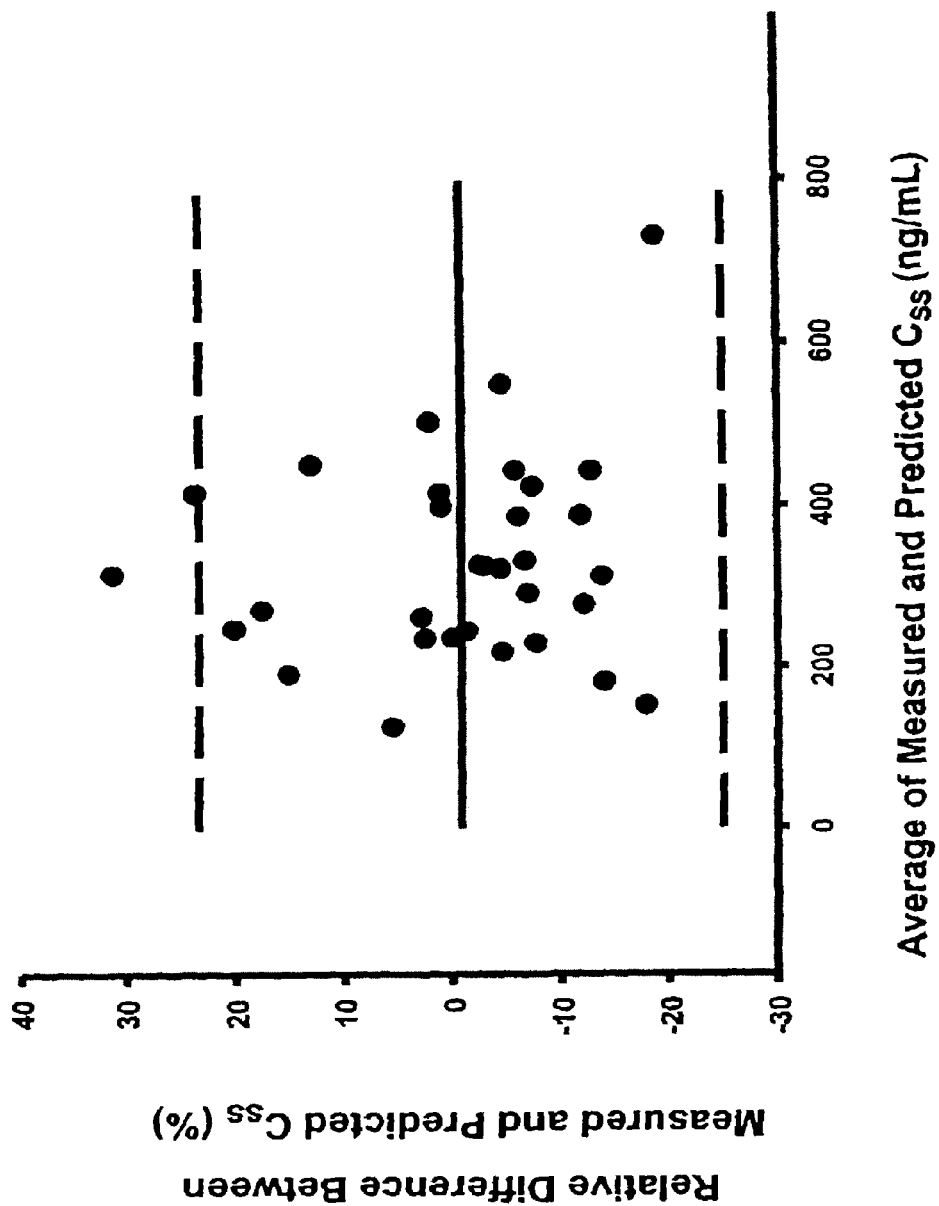
FIG. 3 shows bland-Altman analysis of the correlation between predicted and measured $C_{SS}$. Because a plot of predicted versus measured $C_{SS}$ often do not reveal a systematic under or over estimation (bias), a Bland-Altman analysis was conducted. The averages of the measured and predicted values (abcissa) are plotted against the relative difference in the two values (ordinate). The solid line is the mean value for the relative difference ($-0.8\pm12.2\%$; mean$\pm$SD) and the dotted lines represent the 95% confidence intervals for the data. This plot clearly demonstrates that there is no significant bias associated with this method of prediction.
Figure 4:
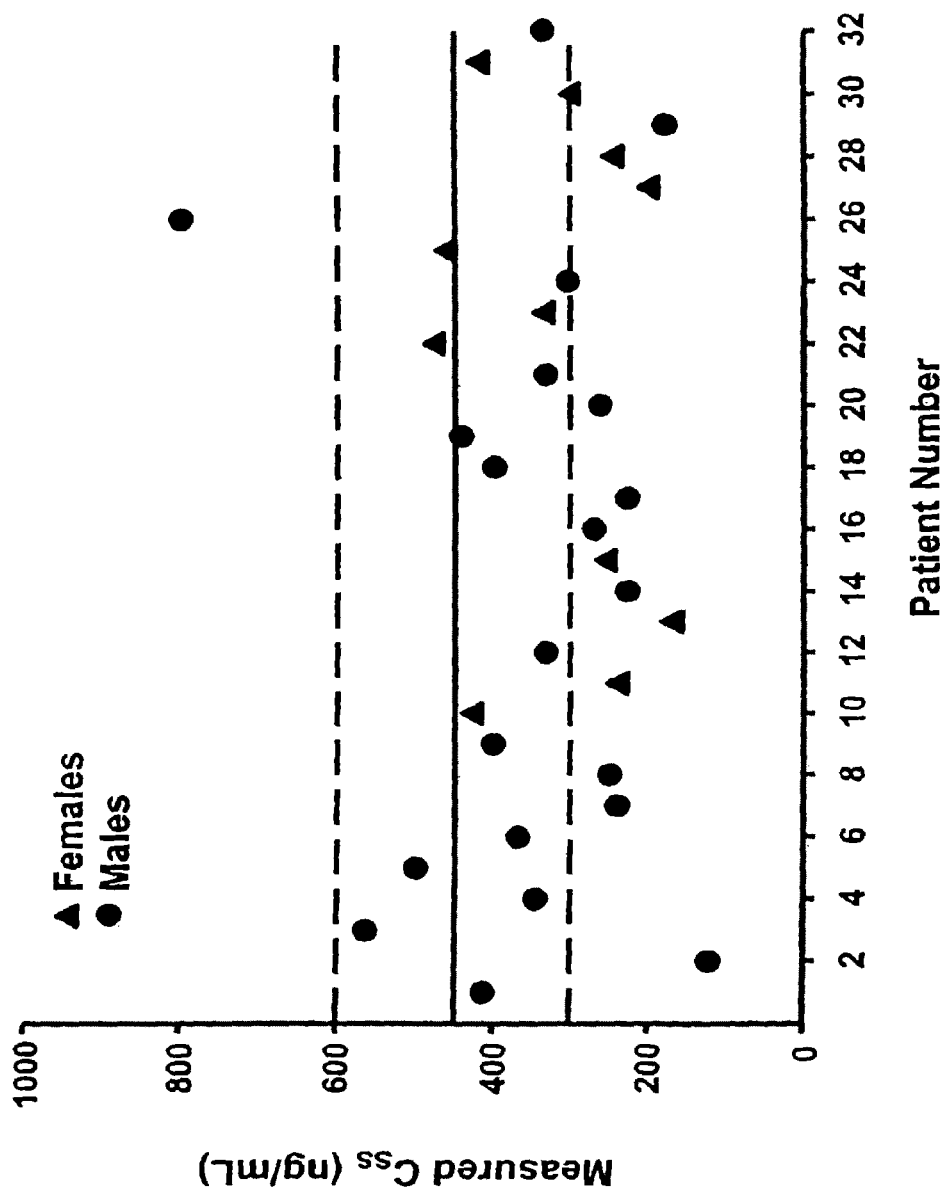
FIG. 4 shows $C_{SS}$ values a consistently lower than those predicted based on previously reported pharmacokinetic parameters. Measured $C_{SS}$ for the 21 males (solid circles) and 11 females (solid triangles) are individually plotted. The solid and dotted lines represent our original target concentrations of 450$\pm$100 ng/mL. These data clearly demonstrate that in TBI patients, $C_{SS}$ values are significantly lower than predicted using pharmacokinetic parameters previously reported.

Table 2 is a summary of the demographic and primary pharmacokinetic data stratified by sex. There were no significant differences between males and females with respect to any of the parameters in Table 2 with the exception of body weight. As one might expect, the mean body weight for the males (81.5±16.2 kg) was significantly greater (p<0.003) than that for the females (63.9±11.0 kg). Clearance (CL) values were calculated from the total dose of progesterone infused and the $AUC_{(0-72\ h)}$ rather than from $AUC_{(0-\infty)}$ because complete post-infusion blood sampling was not possible in a number of the patients for medical reasons. The mean value for CL was found to be 1.73±0.72 L/kg/h and was not different in males(1.66±0.67 L/kg/h) and females (1.88±0.81 L/kg/h). Although a direct comparison is not possible because we did not record heights in our patients and therefore could not calculate body surface areas, CL values in the current study are higher than expected from those reported for progesterone infusions in cancer patients (Christen et al. (1993) *Journal of Clinical Oncology* 11(12):2417-2426). Using the value for progesterone CL from the current serum concentration-time data did not result in any statistically significant differences between the $C_{ss}$ values predicted by $R_o$/CL (332+121 ng/mL) and those actually measured (337±135 ng/mL) and were not different for either males or females. FIG. 2 is a summary of measured and predicted $C_{ss}$ values plotted against the line of identity. The Spearman Rank correlation coefficient for this relationship was 0.946 (p<0.001). The significance of the relationship was confirmed using a Bland-Altman analysis which revealed no systematic bias between the measured and predicted $C_{ss}$ values. The relative difference between predicted and measured $C_{ss}$ was −0.8±12.2% (mean±SD) (See FIG. 3). FIG. 4 is a plot of measured $C_{ss}$ for each patient showing these concentrations were systematically lower than the target concentration range predicted from previous studies (Christen et al. (1993) *Journal of Clinical Oncology* 11(12):2417-2426; Allolio et al. (1995) *European Journal of Endocrinology* 133(6):696-700).

These data suggest that in trauma patients with moderate to severely head injuries the resulting hyperkinetic physiologic state results in a clinically significant increase in progesterone clearance. These data suggest that to achieve our target concentration of 450±100 ng/mL, the maintenance infusion rate should be increased from 0.5 mg/kg/h to approximately 0.8 mg/kg/h.

The mean value for terminal half-life was found to be 1.78±1.0 h. Once again, there were no differences between males (1.60±0.95 h) and females (2.03±1.08 h) (p<0.4). These values are somewhat longer than those reported in cancer patient (Christen et al. (1993) *Journal of Clinical Oncology* 11(12):2417-2426). Volumes of distribution ($V_d$) in the current study are higher than expected from previous reports because of the elevation in CL and decrease in terminal elimination phase rate constant. Although values for males tended to be lower, $V_d$'s were not significantly different for males (3.76±2.14 L/kg) and females (5.76±4.21 L/kg) (p<0.22).

consequently, rising intracranial pressure (Chesnut, et al. (1993) *Journal of Trauma-Injury Infection & Critical Care*, 34(2):216-22; Povlishock and Jenkins (1995) *Brain Pathology*, 5(4):415-26). The treatment of traumatic brain injury is predominantly supportive in nature, and revolves around efforts to maintain cerebral perfusion pressure and adequate oxygenation (Brain Trauma Foundation (1996) "Guidelines for the Management of Severe Head Injury," *Journal of Neurotrauma*, 13(11):643-5; Brain Trauma Foundation B (2000) "Management and Prognosis of Severe Traumatic Brain Injury, Parts I & II," *Journal of Neurotrautna*, 17(June/July): 449-627).

A substantial and rapidly growing body of data indicates that the hormone progesterone, a neurosteroid that is naturally found in the brains of men and women, has potent neuroprotective properties. The data presented herein obtained during the first pilot, randomized controlled clinical trial of progesterone for treatment of moderate to severe acute traumatic brain injury (TBI). In addition to testing whether

TABLE 2

Individual progesterone pharmacokinetic parameters in TBI patients.

| Patient | Sex | Age | BW (kg) | GCS | CL (L/kg/h) | $t_{1/2}$(h) | Vd (L/kg) | Css Measured ng/mL | Css Predicted ng/mL | Corrected Ro mg/kg/h |
|---|---|---|---|---|---|---|---|---|---|---|
| 1 | F | 25 | 72 | 7 | 1.04 | 2.70 | 4.04 | 423 | 482 | 0.47 |
| 2 | F | 29 | 65 | 8 | 2.11 | 2.56 | 7.78 | 234 | 240 | 0.95 |
| 3 | F | 20 | 57 | 11 | 3.60 | | | 166 | 139 | 1.62 |
| 4 | F | 22 | 50 | 6 | 1.68 | 0.92 | 2.24 | 249 | 297 | 0.76 |
| 5 | F | 48 | 73 | 11 | 1.20 | | | 472 | 416 | 0.54 |
| 6 | F | 21 | 70 | 4 | 1.58 | 1.20 | 2.73 | 331 | 317 | 0.71 |
| 7 | F | 19 | 85 | 7 | 1.16 | | | 457 | 432 | 0.52 |
| 8 | F | 53 | 50 | 7 | 2.95 | 2.43 | 10.35 | 195 | 170 | 1.33 |
| 9 | F | 20 | 55 | 7 | 2.25 | 3.64 | 11.83 | 240 | 222 | 1.01 |
| 10 | F | 54 | 57 | 4 | 1.91 | | | 296 | 262 | 0.86 |
| 11 | F | 24 | 69 | 6 | 1.19 | 0.77 | 1.33 | 415 | 420 | 0.54 |
| Mean ± | | 30 | 63.9 | 7* | 1.88 | 2.03 | 5.76 | 316 | 309 | 0.85 |
| SD | | 14 | 11.0 | 4-11** | 0.81 | 1.08 | 4.21 | 110 | 115 | 0.37 |
| 1 | M | 52 | 75 | 6 | 1.37 | 1.14 | 2.25 | 412 | 366 | 0.61 |
| 2 | M | 24 | 70 | 8 | 3.84 | 0.73 | 4.05 | 123 | 130 | 1.73 |
| 3 | M | 47 | 93 | 12 | 0.93 | | | 563 | 538 | 0.42 |
| 4 | M | 25 | 70 | 11 | 1.55 | | | 345 | 323 | 0.70 |
| 5 | M | 23 | 80 | 6 | 0.98 | 3.30 | 4.67 | 499 | 510 | 0.44 |
| 6 | M | 29 | 70 | 12 | 1.07 | 1.77 | 2.73 | 368 | 467 | 0.48 |
| 7 | M | 20 | 65 | 10 | 2.10 | 2.78 | 8.43 | 238 | 238 | 0.95 |
| 8 | M | 18 | 59 | 6 | 2.04 | 1.70 | 5.01 | 248 | 245 | 0.92 |
| 9 | M | 62 | 66 | 6 | 1.33 | 2.20 | 4.22 | 400 | 376 | 0.60 |
| 10 | M | 76 | 84 | 7 | 1.55 | | | 332 | 322 | 0.70 |
| 11 | M | 33 | 100 | 4 | 2.33 | | | 225 | 215 | 1.05 |
| 12 | M | 25 | 87.7 | 6 | 1.36 | | | 268 | 368 | 0.61 |
| 13 | M | 43 | 112.6 | 8 | 1.81 | 1.44 | 3.77 | 225 | 276 | 0.82 |
| 14 | M | 18 | 73 | 5 | 1.24 | | | 398 | 402 | 0.56 |
| 15 | M | 46 | 84 | 11 | 1.22 | | | 441 | 410 | 0.55 |
| 16 | M | 42 | 75 | 7 | 1.87 | 0.60 | 1.62 | 260 | 268 | 0.84 |
| 17 | M | 34 | 122 | 9 | 1.54 | 0.37 | 0.82 | 332 | 324 | 0.69 |
| 18 | M | 42 | 70 | 8 | 1.77 | | | 303 | 283 | 0.80 |
| 19 | M | 65 | 100 | 4 | 0.76 | | | 800 | 662 | 0.34 |
| 20 | M | 33 | 75 | 12 | 2.41 | | | 178 | 207 | 1.09 |
| 21 | M | 42 | 80 | 7 | 1.71 | | | 335 | 292 | 0.77 |
| Mean ± | | 38 | 81.5# | 7* | 1.66 | 1.60 | 3.76 | 347 | 344 | 0.75 |
| SD | | 16 | 16.2 | 4-12** | 0.67 | 0.95 | 2.14 | 148 | 125 | 0.30 |

*Median;
**Range;
p < 0.003 between males and females

Discussion

Clinicians have long sought an effective neuroprotective agent to give to patients shortly following a traumatic brain injury. The pathophysiology of brain injury is well understood, but researchers have not identified a drug that can reliably modulate the pathophysiologic cascade of deleterious effects that lead to cellular necrosis, cerebral edema, and the drug is safe and efficacious for this condition, we sought to determine the pharmacokinetic properties of intravenous progesterone in multi-system trauma patients.

The major findings of our investigation are: 1) A solution of progesterone in 95% ethyl alcohol is stable for up to 2 years at room temperature; 2) Intralipid® solutions containing progesterone in 95% ethyl alcohol are stable for a minimum of 24 hours; 3) A $C_{SS}$ of progesterone can be rapidly achieved and maintained in acute, critically ill traumatic brain injured patients with multi-system trauma using a two phase intravenous infusion paradigm; 4) Progesterone $C_{SS}$ values can be accurately predicted from AUC data; 5) The hyperkinetic physiologic alterations accompanying acute traumatic brain injury result in significant elevations in CL, $t_{1/2}$, and $V_d$ for progesterone; 6) Acute traumatic brain injury, per se, does not result in endogenous release of progesterone; and 7) Alterations in progesterone pharmacokinetics following acute traumatic brain injury are not gender dependent. One of the most important goals in clinical pharmacokinetics is obtaining patient specific estimates of the appropriate pharmacokinetic parameters. The use of model independent methods (AUC) is extremely robust for determining patient specific CL. CL is the primary parameter of interest when drugs are being administered by continuous intravenous infusion, since the resultant patient-specific $C_{SS}$ is dependent only on infusion rate and CL. The current study demonstrates that stable $C_{SS}$ values of progesterone were rapidly achieved with intravenous administration, making dosing adjustments to realize a target concentration practical in a population of critically injured patients regardless of gender. While the number of patients in this investigation receiving a placebo infusion is small, repeated sampling and analysis shows that the initial progesterone concentrations are constant over the 84-hour time course of study. These data suggest that endogenous secretion of progesterone is not significantly stimulated by traumatic brain injury, per se. The ultimate goal, of course, is to define the $C_{SS}$ that correlates with optimum treatment efficacy. Once the pharmacodynamic relationship between steady state serum concentration of progesterone and clinical outcome is elucidated, the parameters determined in our study may be used to draft an infusion paradigm that optimizes the odds of survival and functional recovery. Since the $C_{SS}$ are rapidly achieved and are stable, patient-specific adjustments in infusion rate to maintain a target concentration should be possible with minimal early blood sampling. If such a pharmacologic intervention proves efficacious, our stability data demonstrate that stock solutions of progesterone in ethanol, which are tedious to prepare, can be safely used for up to two years. This would allow neurotrauma units immediate access to progesterone solutions and facilitate rapid treatment implementation.

In 1993, the Brain Injury Foundation convened an international task force to develop evidence-based guidelines for treatment of traumatic brain injury (Brain Trauma Foundation (1996) "Guidelines for the Management of Severe Head Injury," *Journal of Neurotrauma*, 13(11):643-5; Brain Trauma Foundation B (2000) "Management and Prognosis of Severe Traumatic Brain Injury, Parts I & II," *Journal of Neurotrauma*, 17(June/July):449-627; Roberts, et al. (1998) *J Neurol Neurosurg Psychiatry*, 65(5):729-33). With the exception of mannitol and barbiturates, no phattnacological agents were identified that enhance recovery.

In the current study, additional drugs were co-administered to optimize the medical management of these critically injured patients. The drug combinations and dosing regimens were individualized on a patient-specific basis. As such, there was not a consistent group of these drugs given to all patients. While a number of the additional drug classes, in particular, the anticonvulsants and barbiturates can result in altered physiology including increases in hepatic blood flow and increases in oxidative metabolism, we cannot unequivocally determine whether the increased values for progesterone clearance are a result of concomitant drug administration, or traumatic brain injury. Finally, because the drug is available in generic forms it is inexpensive.

Using the results from this study coupled with future findings from a dose response efficacy trial, investigators will be able to adjust infusion rates of progesterone to achieve optimal steady-state concentrations. If intravenous infusion of progesterone proves to produce benefits in acutely brain-injured humans it will represent a major advance in the treatment of this common and devastating condition.

Example 2

A pilot phase II, randomized, double-blind, controlled trial of progesterone for the treatment of a traumatic brain injury was preformed. The administration protocol was carried out was described above in Example 1.

To determine if a therapeutic response was achieved, the following endpoints were monitored:

ICP reduction determined by calculating "therapeutic intensity level" (ICP-TIL);

duration of coma (injury to awaking);

mortality one-month post injury;

neurological outcome 1 month and 1 year post-injury, as determined by Glasgow outcome scale (GOS), Disability rating scale (DRS) and Galveston orientation and amnesia test (GOAT).

The preliminary evaluations are as follows. One hundred patients having moderate to severe TBI were enrolled in the study, which had a randomized block design 4:1 enrollment. Three days IV administration of progesterone [450+/−nmol/L] in both males and females. The administration protocol and pharmaceutical composition administered are described in detail in Example 1. Follow up regarding condition occurred at 30 days and 1 year.

Control subjects has a 30.4% mortality rate, while subjects having the progesterone treatment had a 12.9% mortality rate. The progesterone treatment group also had a 60% reduction in brain deaths. Table 3 summarizes the results.

TABLE 3

| Death Frequency percent | Treatment | | |
|---|---|---|---|
| row Pct Col Pct | A | B | Total |
| Medicinal death | 5 | 2 | 7 |
|  | 5.05 | 2.02 | 7.07 |
| Brain death | 4 | 5 | 9 |
|  | 4.04 | 5.05 | 9.09 |
| Not Dead | 67 | 16 | 83 |
|  | 67.68 | 16.16 | 83.84 |
| Total | 76 | 23 | 99 |
|  |  |  | 100.00 |

For test of significance in Table 3, the $\chi^2$ test with 2 df was significant (p=0.0471). When the treatment groups were compared with respect to the proportion of subjects experiencing brain death (vs. those who experience medical death of who are not dead), we find that the group A has a significantly lower proportion than the B group (p=0.0295 by Fisher's exact test). When the treatment groups with respect to proportion of subjects experiencing medical death (vs. those who experience brain death or who are not dead), it was found that the groups are not statistically significant (p=0.6622 by Fisher's exact score).

Example 3

We conducted a clinical trial to assess the safety of progesterone as a treatment for acute TBI. This phase II, randomized, double blind, placebo-controlled clinical trial was conducted at an urban, level I trauma center. 100 adults presenting within 11 hours of a blunt TBI with a Glasgow Coma Scale score of 4-12 were enrolled with proxy consent. Subjects were randomized on a 4:1 basis to progesterone versus placebo. Blinded observers closely monitored patients for the occurrence of adverse events, and initial functional outcomes were assessed 30 days post-injury. The primary safety outcome was difference in adverse event rates, including mortality. The primary measure of activity was dichotomized Glasgow outcome scale extended (GOSE) 30 days post injury. Seventy-seven patients received progesterone; 23 received placebo. The groups had very similar demographic and clinical characteristics. With the exception of mortality, the rate of adverse events was similar in both groups. Laboratory values and physiological parameters were similar as well. No serious adverse events were attributed to progesterone. GOSE and other measures of neurological outcome were not significantly different between groups, but progesterone-treated subjects had a lower all-cause 30 day mortality rate than controls (rate ratio 0.43; 95% confidence interval 0.18-0.99). In this pilot study progesterone caused no observable harms and showed promising signs of activity for treating TBI.

Introduction

Between 1.5 to 2 million Americans sustain a TBI each year. In the U.S. alone, TBI is annually responsible for 50,000 deaths, 235,000 hospitalizations, and 80,000 cases of long term disability. Approximately 37,000 of these victims experience moderate disabilities (Thurman (2001) "The epidemiology and economics of head trauma," in *Head Trauma: Basic, Preclinical, and Clinical Directions*, ed. Miller (Wiley and Sons); Kraus (1997) "Epidemiology of head injury," in *Head Injury*, ed. Cooper (2nd ed, Williams & Wilkins Co., Baltimore); Solecki et al. (1982) *Australian & New Zealand Journal of Surgery* 52(1):93-102; Klauber et al. (1981) *Am J Epidemiol* 113(5):500-509; Max et al. (1991) *Journal of Head Trauma Rehabilitation* 6(2):76-91; Gentleman et al. (1992) *Injury* 23(7):471-474; Jones et al. (1994) *Journal of Neurosurgical Anesthesiology* 6(1):4-14.; Cohadon et al. (1991) *Journal of the Neurological Sciences* 103 Suppl:S27-31; and, Sakata et al. (1991) *Brain Injury* 4:411-419.) and 17,000 require specialized care for life. The CDC estimates that 5.3 million Americans are living with disability from TBI. Lifetime costs of TBI are estimated to exceed $56 billion per year (Thurman (2001) "The epidemiology and economics of head trauma," in *Head Trauma: Basic, Preclinical, and Clinical Directions*, ed. Miller (Wiley and Sons)). We conducted a pilot clinical trial to assess the safety and potential efficacy of administering intravenous progesterone to victims of moderate to severe acute traumatic brain injury.

Methods

Study Design: The primary objective of this phase II randomized, double blind, placebo-controlled trial was to assess potential harms of administering intravenous progesterone to acutely brain-injured patients of both sexes. We also hoped to detect signals of activity.

In the US, IV progesterone had been authorized for experimental use in only three previous clinical studies, none of which were related to TBI (Aebi et al. (1999) *Cancer Chemotherapy & Pharmacology* 44(3):259-265; Allolio et al. (1995) *European Journal of Endocrinology* 133(6):696-700; and, Christen et al. (1993) *Journal of Clinical Oncology* 11(12):2417-2426). The present study shows that IV administration of progesterone following TBI would not result in an increased rate of adverse or serious adverse events.

According to the U.S. Food and Drug Administration, an "adverse event" is any undesirable medical event occurring to a subject in a clinical trial, whether or not related to the study drug. This includes events not seen at baseline, or worsened if present at baseline. "Serious adverse events" are defined as death, immediate risk of death, or suspicion that use or continued use would result in the patient's death, prolongation of existing hospitalization, persistent or significant disability/incapacity, or a congenital anomaly/birth defect.

To detect adverse events, blinded observers screened each study subject on a daily basis to identify a wide range of adverse events, including but not limited to those that that could be plausibly related to progesterone administration. These included any thromboembolic event (deep vein thrombosis, thrombophlebitis, ischemic myocardial infarction, pulmonary embolism, stroke or transient ischemic attack), elevated liver enzymes, temperature elevation, allergic reactions, and hyperglycemia. All laboratory test results obtained during the course of treatment were recorded and analyzed to detect abnormal levels or worrisome trends. An independent internal safety monitor made the determination if an adverse event was associated with study treatment. Both the FDA and an independent NIH-appointed data safety monitoring board independently reviewed these determinations.

In addition to monitoring subjects for signs of harm, we hoped to detect signals of activity. We hypothesized that treatment with progesterone might reduce 30 day mortality and improve a number of short term outcomes following TBI. For this preliminary study, our primary outcome of interest was Glasgow Outcome Scale Extended (GOSE) 30 days post-injury. Other outcome measures at 30 days included group mortality, Disability Rating Scale score, duration of coma, duration of post-traumatic amnesia, and control of increased intracranial pressure.

Setting: The study was conducted at an urban public hospital with over 100,000 patients visits per year, the regions only level I trauma center serving a metropolitan population of more than 4 million.

Figure 5:
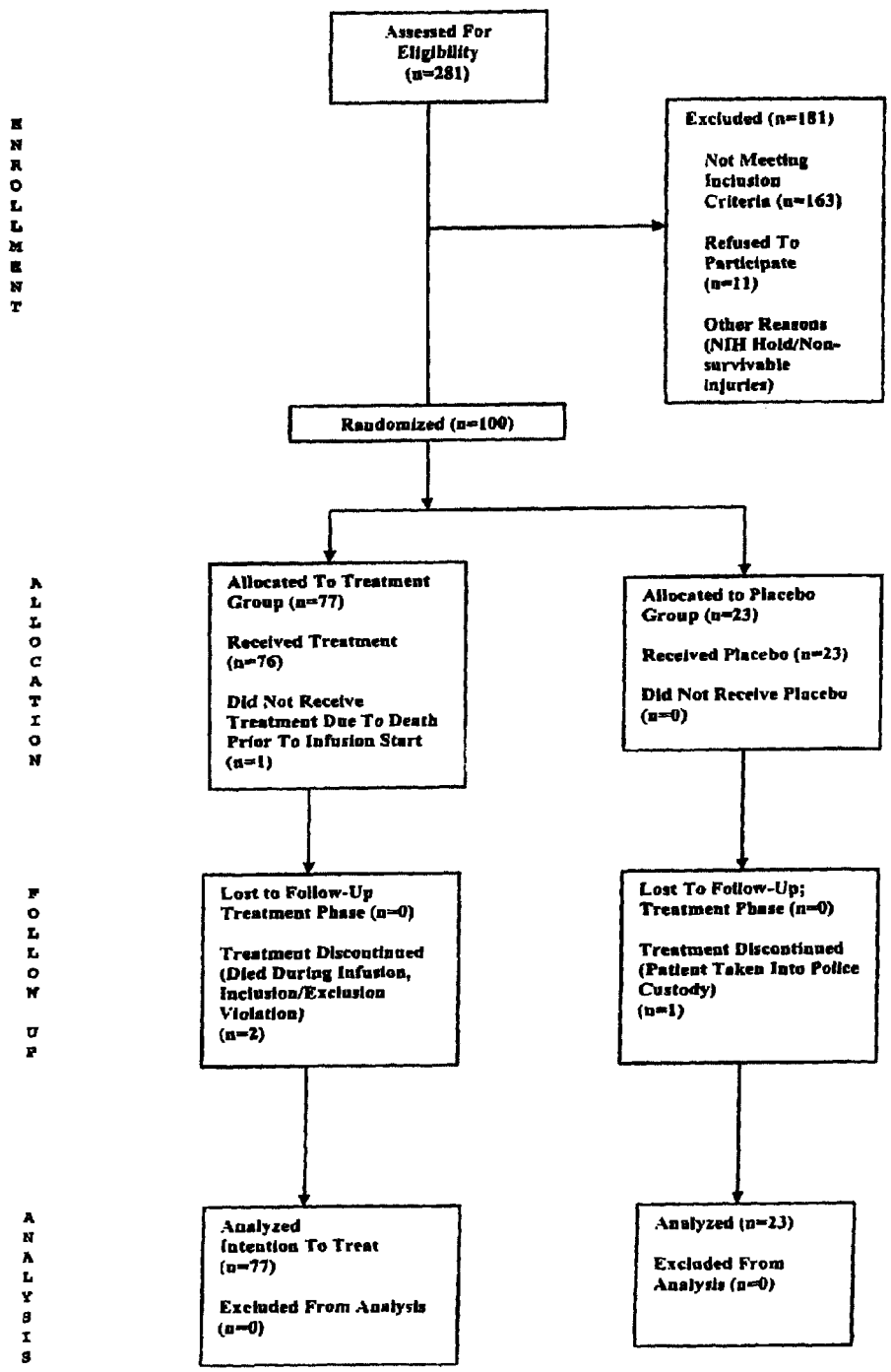
FIG. 5 provides a schematic of the enrollment protocol for the selection of patient for the TBI study.

Selection of participants: Consecutive adult victims of blunt TBI who reached Grady within 11 hours of injury with a post-stabilization or "index" Glasgow Coma Scale score (iGCS) of 4-12 were eligible for enrollment (FIG. 5). Only 3 potentially eligible patients were missed during the 2.5-year enrollment period (May 28, 2002 and Sep. 17, 2004).

Whenever a potential candidate was identified, a study investigator came to the emergency department within 30 minutes to assess eligibility. Exclusion criteria included a blood alcohol concentration of >250 mg/dl; penetrating brain injury; age<18 years; an iGCS of <4 or >12; indeterminate time of injury; pregnancy; cancer; stroke; spinal cord injury; or unable to secure proxy consent within 11 hours of injury.

Because patients could not consent for themselves, a legally authorized representative was approached. Proxies were informed of the study's rationale, design, and anticipated benefits and risks. They were assured that participation was voluntary, and nonparticipation would not affect the patient's care. To facilitate comprehension, our consent form was drafted at an $8^{th}$ grade reading level. A Spanish language version was produced as well. An investigation new drug authorization to use intravenous progesterone to treat TBI was obtained from the U.S. Food and Drug Administration, and a NIH-appointed DSMB provided independent guidance and oversight. The hospital's Research Oversight Committee and the University's Institutional Review Board approved our study. Before initiating enrollment, we briefed leaders of several local advocacy organizations. We also convened a community advisory board.

Interventions: Following proxy consent, patients were placed in one of 8 clinical subgroups defined by gender (male versus female), race (black versus all others) and TBI severity (moderate versus severe). Within each subgroup, permuted block randomization was employed to assign 4 out of every 5 consecutive patients to progesterone and the other to placebo (4:1 randomization). This asymmetric approach was adopted at the request of our NIH-appointed DSMB to maximize the number of patients receiving study drug while maintaining blinding.

To insure blinding of all personnel at the hospital, including the hospital pharmacists mixing study infusions, drug kits were prepared off-site by an Investigational Drug Center. Vials of the study drug and placebo were identical in appearance and physical properties. To produce a set of vials, progesterone was dissolved in 95 percent ethanol and filtered into sterile vials using a 0.2µ filter. Aliquots were assayed to confirm uniform concentration and sterility. Each study kit contained either 6 vials of progesterone in ethanol (treatment) or 6 vials of ethanol alone (placebo).

Whenever a patient was enrolled, the next kit in sequence for that subgroup was used to prepare infusions. The first vial was mixed in Intralipid™ 20% to deliver a one-hour loading dose of 0.71 mg/kg of progesterone at a standard rate of 14 mls/hour, followed by a maintenance infusion of 0.5 mg/kg/h at a standard rate of 10 mls/hour. The remaining vials were used to prepare 5 subsequent 12-hour infusions at the same standard rate of 10 mls/hour for a total of 3 days of treatment. Details of drug monitoring are reported elsewhere (Wright et al. (2005) *J Clin Pharmacol* 45(6):640-648).

Clinical services treating brain injured patients at our hospital follow a consensus protocol based on the guidelines of the Brain Trauma Foundation (Brain Trauma Foundation B (2000) *Journal of Neurotrauma* 17(June/July):449-627). This protocol governs the treatment of TBI patients from pre-hospital settings to hospital discharge. A rigorous, stepwise approach is specified to treat episodes of increased intracranial pressure (ICP). Adopting this protocol assured that with the exception of treatment group assignment, all study participants received standard treatment for TBI.

Methods of Measurement: To assess drug safety, study personnel rounded daily to document the occurrence of adverse events (AEs) or serious adverse events (SAES). Hourly vital signs (blood pressure, heart rate, respiratory rate, temperature, and pulse oximetry), intracranial pressure readings, and other parameters (mean arterial pressure, cerebral perfusion pressure, and fluid balance), were abstracted from each patient's chart. Laboratory values were obtained from the hospital's information system, and concomitant medications and interventions were noted.

Whenever an SAE occurred, an independent board-certified neurosurgeon assessed its potential relationship to study treatment using pre-defined scale. SAEs were reported within 24 hours to the Institutional Review Board (IRB), our NIH-appointed Data Safety Monitoring Board (DSMB), and the U.S. Food and Drug Administration. All other adverse events were reported to on a weekly basis.

The infusion was stopped if a patient experienced an anaphylactic reaction, a major thromboembolic event, an unexplained elevation of serum aspartate aminotransferase (AST) or alanine aminotransferase (ALT) to a level greater than 5,000 IU, or a serum total bilirubin level greater than 10 mg/dl. We agreed to prematurely halt enrollment if either of 2 interim analyses revealed that one group or the other experienced a significantly higher rate of SAEs, including mortality, than the other. These rules were based on O'Brien-Fleming boundaries (O'Brien and Fleming (1979) *Biometrics* 35(3): 549-556), constructed using an alpha spending approach (DeMets and Lan (1994) *Statistics in Medicine* 13(13-14): 1341-1352; discussion 1353-1346).

To determine if the study drug had a beneficial impact on patients, we collected a variety of physiological and functional measures. These included: hourly intracranial pressure measurements; duration of coma, defined as the number of hours from injury to awakening (GCS>8 or motor score >5), and duration of post-traumatic amnesia, defined as the number of days until a subject achieved two consecutive Galveston Amnesia and Orientation test scores of 75 or better. Thirty days following each injury event, we assessed each patient's Glasgow Outcome Score Extended (GOSE) and Disability Rating Scale (DRS). Patients who were severely impaired were classified as "not testable"—a surrogate marker for a poor outcome. Reliability codes were used to record reasons for non-administration of a particular measure, such as physical impairment (e.g., hemiparesis) cognitive impairment (e.g., could not understand instructions), or intoxication. One-year outcomes will be reported at a later date.

Data collection and processing: Data collection was guided by a formal data management plan and standard operating procedures manual. Data collected at the bedside were recorded on paper case report forms (CRFs) and subsequently double entered into a web-based ORACLE® database. Entered CRFs were not accepted as valid unless the double entries matched and all range checks were met. Special edit queries were constructed to generate transport files for importing into SAS® for analysis.

Outcome Measures: The primary aim of our study was to assess the safety of treatment with progesterone. We hypothesized that treatment and control groups would experience similar rates of SAE's and AE's. Our secondary aim was to look for signs of drug activity by assessing several measures of outcome. Our a priori primary measure of outcome was the Glasgow Outcome Scale-Extended (GOSE) (Teasdale et al. (1998) *Journal of Neurotrauma* 15(8):587-597). Other outcome measures included: 1) death within 30 days of injury 2) duration of coma (Levin (1995) *Journal of Neurotrauma* 12(5):913-922); 3) duration of post-traumatic amnesia (Levin et al. (1979) *Journal of Nervous & Mental Disease* 167(11): 675-684); 4) mean intracranial pressure and intracranial pressure therapeutic intensity level (ICP-TIL) (Maset et al. (1987) *Journal of Neurosurgery* 67(6):832-840) and 5) the Disability Rating Scale (DRS) (Hall et al. (2001) *Arch Phys Med Rehabil* 82(3):367-374).

Primary Data Analysis—Treatment and placebo groups were compared with respect to a variety of demographic, historical and prehospital characteristics to ensure that important independent predictors of outcome were equally distributed. Next, the groups were compared with respect to rates of adverse and serious adverse events, using Fisher's exact test. Generalized linear model analysis using a negative binomial distribution was used to compare rates of events that occurred multiple times per patient within the first 30 days (McCullagh and Nelder (1989) *Generalized Linear Models* (2nd ed, Chapman & Hill)). Then, group specific differences in 30-day outcomes. Fisher's exact test was used to analyze GOSE scores dichotomized into "good or moderate recovery" versus all other levels. Wilcoxon's rank sum test was used to compare group specific DRS scores. Mean and median durations of coma and post-traumatic amnesia were compared using student's t-test. All analyses were stratified on an a priori basis by brain injury severity (iGCS 4-8 (severe) versus iGCS 9-12 (moderate)). Longitudinal mixed effects models were used to analyze ICP-TIL as well as other hourly or daily clinical measurements from enrollment through treatment day 4.

To insure that any observed differences in mortality were associated with the study treatment rather than confounding clinical factors, additional multivariate analyses were performed. Variables determined to be independently associated with all-cause mortality or CNS related-death, such as iGCS (dichotomized into moderate versus severe), injury severity score and Marshall CT score were incorporated in a stepwise logistic regression analyses. Because GCS often fluctuates during the first few hours after injury, additional stepwise logistic regressions were performed using dichotomized GCS 1 day post-injury.

Results

Screening and Enrollment—A total of 281 patients were screened. Three potentially eligible patients were missed and 18 patients could not be enrolled because their identity was unknown or a proxy could not be contacted within 11 hours of injury. Six potentially eligible patients who presented during one of 3 procedural "holds" could not be enrolled. One patient was excluded after consent but prior to randomization because the treating team decided that his injuries were non-survivable. Eleven eligible patients were not enrolled because their proxy declined to consent. (FIG. 1) Non-participants resembled participants with respect to gender, race, and mechanism of injury.

Characteristics of study subjects—Seventy-one patients were male; 34 were black. Mean age was 36 years. Seventy-two patients (72%) had an iGCS of 4-8; the remainder had a score of 9-12. More than 80% of injuries were caused by a motor vehicle crash or a fall. Most patients reached the hospital within an hour of injury; 58 percent by helicopter. Because it frequently took several hours to locate a representative for proxy consent, mean time from injury to initiation of study infusion was 6.3 (95% CI 5.9-6.8) hours in the progesterone group and 6.2 (95% CI 5.9-6.6) hours in the placebo group.

Randomization—77 subjects were randomized to progesterone; 23 to placebo. Treatment groups were highly similar with respect to gender, age, race, iGCS, mechanism of injury, revised trauma score, injury severity score, time from injury to E.D. arrival, time to study treatment, Marshal CT score (Marshall et al. (1991) *J Neurosurgery* 75 (suppl):S14-20), and E.D. disposition (Table 4).

Dosing and protocol compliance—Our pharmacokinetic findings are reported elsewhere (Wright et al. (2005) *J Clin Pharmacol* 45(6):640-648). One patient randomized to progesterone died before the study drug could be initiated. She was retained in our analysis under the principle of "intention to treat." All other members of the treatment group and no members of the control group had high serum levels of progesterone in their sera during drug administration. Minor protocol violations, such as brief delays in changing I.V. bags, were common. Sufficient solution was provided to prevent these from interrupting infusion.

Six major protocol violations occurred. Four involved prolonged interruptions of the infusion, one involved a dosing error, and one involved inappropriate enrollment of a motor vehicle crash victim. When a repeat CT scan on the second hospital day revealed an ischemic stroke, his progesterone infusion was promptly stopped. Subsequent review of the admission CT scan showed subtle but clear signs of the stroke, which was traced to a traumatic carotid artery dissection. Because the stroke predated treatment, this incident was classified as a major protocol violation rather than a SAE.

Safety—Aggregate and individual rates of adverse and serious adverse events were not different between groups (Table 5). This was true whether AEs and SAEs were analyzed by any occurrence or by mean episodes per subject. Laboratory values of the treatment groups were remarkably similar, whether analyzed by group means or the frequency with which a specified test value exceeded pre-specified thresholds. Progesterone-treated subjects experienced a significantly lower rise in mean temperature over the infusion interval compared to controls. This was determined by analyzing a treatment by time interaction teun for progesterone versus control patients, with the slope=−0.0055 (95% CI, −0.010 to −0.001).

The only adverse events specifically ascribed to administration of progesterone were two cases of superficial phlebitis at the IV site. Both resolved spontaneously. Three patients, all of whom received progesterone, developed a deep vein thrombosis between 6 to 23 days following completion of the infusion. All 3 cases were treated without incident. Two patients suffered ischemic strokes. One in a patient randomized to progesterone, occurred prior to treatment and was considered a major protocol violation. The other involved a patient randomized to placebo. A patient randomized to progesterone sustained a myocardial infarction two days after the study infusion was completed. At the time, he was receiving high-dose neosynephrine in an effort to boost his cerebral perfusion pressure. Post-mortem revealed no intra-coronary thrombosis.

Signals of benefit—During the first 4 days post-injury, mean intracranial pressure levels (ICPs) of progesterone-treated subjects with monitors in place remained stable, while mean ICPs among placebo-treated subjects with ICP monitors in place tended to rise. However, these trends were not statistically significant. Mean ICP-TIL scores did not significantly differ between groups (Table 6).

Severe TBI patients (iGCS 4-8) treated with progesterone remained in coma significantly longer than survivors who received placebo (mean duration 10.1 days (7.7, 12.5) versus 3.9 days (2.5, 5.4) respectively). The mean duration of post-traumatic amnesia did not significantly differ between groups (Table 7). Ten of 77 patients (13 percent) randomized to progesterone died within 30 days of injury, compared to 7 of 23 patients (30.4 percent) randomized to placebo (rate ratio 0.43, 95% CI 0.18-0.99). When the analysis was restricted to the 99 subjects who received treatment, this difference was more significant (rate ratio 0.39, 95% confidence interval 0.16, 0.93). Deaths due to neurological causes tended to be lower in the treatment group than controls (rate ratio 0.30, 95% confidence interval 0.08-1.12) while deaths from non CNS causes did not appreciably differ. The association between treatment group and mortality remained robust in multivariate models, including several based on dichotomized GCS at 24 hours (Table 7).

We were able to contact 92 percent of survivors 30 days post-injury to assess their functional status. Our primary outcome measure, dichotomized GOSE, did not significantly differ between groups. The DRS scores of severely brain injured patients were similar as well. However, moderately brain-injured patients randomized to the study drug achieved significantly better DRS scores, on average, than those randomized to placebo (Table 7).

Discussion

Because progesterone has not been previously used to treat acute traumatic brain injury, we conducted a pilot, phase II study to assess potential harms. Arriving patients were care-fully screened for eligibility. Ninety nine percent of potentially eligible patients were screened, and 90 percent of those who met inclusion criteria were enrolled with proxy consent. Treatment and control patients were well matched by injury severity, time to treatment and other independent predictors of outcome.

The decision to secure proxy consent rather than seek exemption from informed consent delayed initiation of treatment an average of 6.5 hours. Although one animal study has suggested that progesterone may produce beneficial effects as late as 24 hours post-injury, the magnitude of benefit was greatest when treatment was administered within 2 hours of injury (Roof et al. (1996) *Exp Neurol* 138(2):246-251).

Three members of the treatment group developed deep vein thrombosis—the earliest 6 days post-infusion. This frequency is well within our institution's historical incidence of DVT in major trauma patients (unpublished data). With the exception of mortality, treatment and control groups experienced similar rates of AEs and SAEs. They also had very similar lab and physiological values.

Our secondary goal was to detect signs of drug activity. We chose GOSE as our primary outcome measure because it the most widely used standard in the brain injury literature. We observed promising signs of activity.

No differences were found in mean ICP or mean ICP-TILs.

There was no significant difference between treatment groups with respect to duration of post-traumatic amnesia and 30-day GOSE. However, the 30-day mortality rate among subjects randomized to the treatment group was less than half that of the control group. This difference persisted after other important predictors of outcome were taken into consideration.

Severely brain-injured patients in the treatment group had a longer mean duration of coma than those in the control group. This may represent a "survivor effect". If progesterone prevented the deaths of several patients during the 30 day follow up period, it is not surprising that these survivors remained in coma for a longer duration of time. One-year survival and functional outcomes will be reported at a later date.

In retrospect, we would have preferred to enroll patients with exception to informed consent. This would have allowed us to start the study treatment much sooner, and enroll patients who were lost because we could not find a legally authorized representative within the enrollment window. Earlier administration of the study drug might have produced greater evidence of activity. We recognized, however, that this is the first human trial of progesterone in the setting of acute brain injury and our study was primarily designed to assess drug safety rather than activity. This is why we enrolled patients with proxy consent and accepted potentially significant treatment delays (up to 11 hours) to maximize recruitment. Based on our encouraging findings with regards to safety, we hope to conduct a larger trial under the federal regulatory framework that allows exception from consent in limited circumstances (Federal regulations of 21CFR50.24). This will enable earlier initiation of treatment and maximize the opportunity to detect any evidence of neuroprotective effects.

In summary, this study represents an important step in assessing the utility of progesterone for treating acute traumatic brain injury. TBI is a leading cause of death and disability worldwide. No pharmacological agent has been shown to improve outcomes. We previously reported that progesterone can be accurately administered in intravenous form to victims of TBI (Wright et al. (2005) *J Clin Pharmacal* 45(6): 640-648). This analysis offers preliminary evidence that this treatment causes no harm and may have disease-modifying activity. A clinical trial involving more subjects, 1:1 randomization, and a short enrollment window is warranted. If it corroborates our findings, this will represent a major advance in brain injury care.

TABLE 4

Characteristics by Group: Participants in ProTECT ™ (N = 100)

| Characteristic | Overall | Progesterone | Placebo | p-value* |
|---|---|---|---|---|
| Number of Subjects | 100 | 77 | 23 | N/A |
| Mean Age (X ± sd) | 35.8 ± 15.0 | 35.3 ± 14.3 | 37.4 ± 17.4 | 0.54 |
| Male (%) | 71% | 71% | 70% | 0.86 |
| African American (%) | 35% | 34% | 39% | 0.64 |
| Mechanism of Injury (%) | (n = 100) | | | |
| Motor Vehicle | 76 | 74 | 83 | |
| Pedestrian Struck | 3 | 4 | 0 | 0.58 |
| Bicycle | 3 | 3 | 4 | (mvc vs. all |
| Fall | 7 | 6 | 9 | other) |
| Other | 11 | 13 | 4 | |
| Index GCS (% severe) | 72% | 73% | 70% | 0.77 |
| 24 hr GCS (% severe) | 61% | 70% | 50% | 0.23 |
| Injury Severity Score (X ± sd) | 24.2 ± 9.2 | 24.5 ± 9.9 | 23.3 ± 6.4 | 0.50 |
| Revised Trauma Score (X ± sd) | 6.1 ± 0.6 | 6.1 ± 0.6 | 6.2 ± 0.7 | 0.83 |
| Probability of Survival (P ± sd) | 0.9 ± 0.2 | 0.9 ± 0.2 | 0.8 ± 0.1 | 0.53 |
| Initial CT scan Marshall Score[67] (1-5) | 2.8 ± 1.6 | 3.0 ± 0.2 | 2.3 ± 0.3 | 0.09 |
| Time injury to arrival (X ± sd) min | 50.3 ± 30.3 | 49.5 ± 32.3 | 54.3 ± 32.3 | 0.42 |
| Time injury to infusion (X ± sd) min | 379.2 ± 118.0 | 380.7 ± 125.6 | 374.0 ± 91.2 | 0.78 |

*p value = progesterone group versus placebo group

TABLE 5

30-Day Adverse Event Rates by Treatment Group

| | Progesterone (%) | Placebo (%) | Relative Risk (95% confidence interval) |
|---|---|---|---|
| Acute respiratory distress syndrome | 2.6 | 4.4 | 0.60 (0.06, 6.29) |
| Central nervous system infection | 1.3 | 0.0 | — |
| Cardiac Arrhythmia | 5.2 | 17.4 | 0.30 (0.08, 1.10) |
| Cholestatic Jaundice | 6.5 | 0.0 | — |
| Death within 30 days | 13.0 | 30.4 | 0.43 (0.18, 0.99) |
| Fever | 70.1 | 82.6 | 0.85 (0.67, 1.08) |
| Gastrointestinal Bleed | 5.2 | 0.0 | — |
| Hyperglycemia-non DM | 27.3 | 30.4 | 0.90 (0.44, 1.84) |
| Hypertension | 11.7 | 8.7 | 1.34 (0.31, 5.79) |
| Hypotension | 9.1 | 21.7 | 0.42 (0.15, 1.19) |
| Hypothermia | 5.2 | 8.7 | 0.60 (0.12, 3.06) |
| Hypoxemia | 11.7 | 13.0 | 0.90 (0.26, 3.04) |
| Increase Liver Enzyme | 6.5 | 4.4 | 1.49 (0.18, 12.15) |
| Phlebitis at Injection Site | 1.3 | 0.0 | — |
| Rash or Hives | 2.6 | 0.0 | — |
| Syndrome of inappropriate ADH | 1.3 | 0.0 | — |
| Seizures | 5.2 | 0.0 | — |
| Sepsis | 2.6 | 0.0 | — |
| Shock | 2.6 | 0.0 | — |
| Suspected Pneumonia | 11.7 | 4.4 | 2.69 (0.46, 20.12) |
| Tachycardia | 24.7 | 13.0 | 1.89 (0.61, 5.83) |
| Thromboembolic Disease | 3.9 | 0.0 | — |

TABLE 6

Physiological Parameters

| Infusion Day | Progesterone Group | | | Placebo Group | | |
|---|---|---|---|---|---|---|
| DAY | n | mean | 95% CI | n | mean | 95% CI |
| Intracranial Pressure Therapeutic Intensity Level | | | | | | |
| 0 | 16 | 2.6 | 1.9, 3.4 | 5 | 3.8 | 1.9, 5.7 |
| 1 | 27 | 2.7 | 1.4, 4.1 | 9 | 2.7 | 1.3, 4.1 |
| 2 | 26 | 3.2 | 1.9, 4.5 | 10 | 4.5 | 1.2, 7.8 |
| 3 | 17 | 3.7 | 1.1, 6.3 | 9 | 4.2 | 0.6, 7.9 |
| 4 | 15 | 2.8 | 0.6, 5.0 | 5 | 6.0 | 0, 12.3 |
| Intracranial Pressure (mm Hg) | | | | | | |
| 0 | 17 | 16.0 | 12.3, 19.7 | 5 | 13.13 | 8.1, 18.2 |
| 1 | 36 | 17.1 | 12.6, 21.5 | 12 | 14.69 | 10.1, 19.3 |
| 2 | 34 | 15.4 | 13.2, 17.5 | 12 | 17.32 | 12.1, 22.6 |
| 3 | 34 | 16.0 | 13.8, 18.2 | 12 | 18.27 | 13.3, 23.2 |
| 4 | 25 | 17.7 | 14.8, 20.7 | 12 | 19.95 | 13.8, 26.1 |
| Cerebral Perfusion Pressure (mmHg) | | | | | | |
| 0 | 13 | 70.3 | 61.9, 78.8 | 3 | 71.9 | 48.4, 95.4 |
| 1 | 36 | 73.4 | 66.2, 80.6 | 12 | 76.8 | 71.5, 82.0 |
| 2 | 34 | 75.9 | 71.7, 80.1 | 12 | 74.9 | 70.6, 79.1 |
| 3 | 34 | 74.9 | 70.7, 79.2 | 12 | 75.6 | 70.8, 80.4 |
| 4 | 25 | 73.8 | 68.0, 79.6 | 11 | 73.2 | 67.2, 79.1 |
| Systolic Blood Pressure (mmHg) | | | | | | |
| 0 | 68 | 129.4 | 125.6, 133.2 | 18 | 127.6 | 119.2, 136.0 |
| 1 | 76 | 130.2 | 126.5, 133.9 | 22 | 129.9 | 124.0, 135.7 |
| 2 | 75 | 133.5 | 130.2, 136.8 | 23 | 133.0 | 125.9, 140.1 |
| 3 | 75 | 133.8 | 130.1, 137.6 | 22 | 137.0 | 130.6, 143.9 |
| 4 | 73 | 132.7 | 128.6, 136.9 | 21 | 137.8 | 132.5, 143.4 |
| Diastolic Blood Pressure (mmHg) | | | | | | |
| 0 | 68 | 69.5 | 66.6, 72.5 | 18 | 66.6 | 60.3, 72.9 |
| 1 | 76 | 67.4 | 65.1, 69.8 | 22 | 66.4 | 62.6, 70.1 |
| 2 | 75 | 67.2 | 64.8, 69.7 | 23 | 65.7 | 60,7, 70.8 |
| 3 | 75 | 67.5 | 65.3, 69.6 | 22 | 66.4 | 62.2, 70.6 |
| 4 | 73 | 67.3 | 65,2, 69.4 | 21 | 67.3 | 63.6, 71.1 |
| Temperature (degrees centigrade) | | | | | | |
| 0 | 35 | 37.0 | 36.6, 37.4 | 11 | 36.9 | 36.3, 37.6 |
| 1 | 76 | 37.4 | 37.3, 37.6 | 22 | 37.4 | 37.1, 37.7 |
| 2 | 75 | 37.4 | 37.3, 37.6 | 23 | 37.7 | 37.4, 38.0 |
| 3 | 75 | 37.4 | 37.3, 37.5 | 22 | 37.7 | 37.4, 37.9 |
| 4 | 73 | 37.5 | 37.3, 37.6 | 21 | 37.7 | 37.4, 38.0 |
| Fluid Balance (+ mls) | | | | | | |
| 1 | 76 | 767.9 | 312.8, 1223.0 | 23 | 834.7 | 0, 1794.9 |
| 2 | 76 | 1189.5 | 645.9, 1733.0 | 23 | 1282.2 | 583.4, 1981.0 |

TABLE 6-continued

| | | | | | | | |
|---|---|---|---|---|---|---|---|
| 3 | 75 | 802.0 | 401.5, 1202.5 | 22 | 1292.6 | 748.1, 1837.0 | |
| 4 | 75 | 818.7 | 386.3, 1251.2 | 20 | 812.0 | 66.9, 1557.2 | |

Parameters Exceeding Threshold Values
Percent of Patients with Clinical Values Exceeding the Threshold

| | Progesterone Group | | | Placebo Group | | | |
|---|---|---|---|---|---|---|---|
| | n | denominator | % | # | n | % | p-value |
| MAP < 70 | 22 | 76 | 29.0 | 10 | 23 | 43.5 | 0.21 |
| CPP < 60 | 18 | 37 | 48.7 | 5 | 12 | 41.7 | 0.75 |
| ICP > 25 | 12 | 37 | 32.4 | 5 | 12 | 41.7 | 0.73 |
| Systolic BP < 90 | 22 | 76 | 29.0 | 10 | 23 | 43.5 | 0.21 |

Mean Duration of Pressures Exceeding Threshold Values (hours)

| | Progesterone Group | | | Placebo Group | | | |
|---|---|---|---|---|---|---|---|
| Duration (hrs) | n | mean | std error | n | mean | std error | Wilcoxon |
| MAP < 70 | 76 | 2.5 | 0.7 | 23 | 3.4 | 1.40 | 0.24 |
| CPP < 60 | 37 | 6.9 | 2.9 | 12 | 2.4 | 1.18 | 0.56 |
| ICP > 25 | 37 | 5.0 | 2.5 | 12 | 11.3 | 7.88 | 0.46 |
| Systolic BP < 90 | 76 | 2.7 | 0.7 | 23 | 3.5 | 1.40 | 0.25 |

Mean Frequency of Pressures Exceeding Threshold Values

| | Progesterone Group | | | Placebo Group | | | |
|---|---|---|---|---|---|---|---|
| Event | Occurrence | # Consecutive Readings | Rate/1000 consecutive readings | Occurrence | # Consecutive Readings | Rate/1000 consecutive readings | p-value |
| MAP < 70 | 128 | 4334 | 29.5 | 0 | 1477 | 41.3 | 0.81 |
| CPP < 60 | 183 | 1969 | 92.9 | 23 | 816 | 28.2 | 0.41 |
| ICP > 25 | 145 | 2067 | 70.2 | 121 | 828 | 146.1 | 0.61 |
| Systolic BP < 90 | 132 | 4112 | 32.1 | 62 | 1365 | 45.4 | 0.81 |

MAP = mean arterial pressure,
CPP = cerebral perfusion pressure,
ICP = intracranial pressure,
BP = blood pressure

TABLE 7

Outcomes Variables 30 days Post Injury

| | Progesterone Group | Placebo Group |
|---|---|---|
| Total N | 77 | 23 |

Mortality

| | n | % | n | % | Risk Rate Ratio | 95% Confidence Interval |
|---|---|---|---|---|---|---|
| All cause mortality (ITT)* | 10 | 13.0 | 7 | 30.4 | 0.43 | 0.18, 0.99 |
| All cause mortality (TR)# | 9 | 11.8 | 7 | 30.4 | 0.39 | 0.16, 0.93 |
| Neurological deaths# | 4 | 5.3 | 4 | 17.4 | | |
| Non-neurological deaths# | 5 | 6.6 | 3 | 13.0 | | |
| Survived > 30 days# | 67 | 88.2 | 16 | 69.6 | | |

Total and Dichotomized Glasgow Outcome Score - Extended

| Disability level | n | % | % | n | % | % | Risk Rate Ratio | 95% Confidence Interval |
|---|---|---|---|---|---|---|---|---|
| Dead | 10 | 14.2 | | 7 | 31.8 | | | |
| Vegetative State | 5 | 7.1 | | 0 | 0 | | | |
| Lower Severe | 28 | 40.0 | 70.0 | 7 | 31.8 | | 81.8 | |
| Upper Severe | 6 | 8.6 | | 4 | 18.2 | | | |

TABLE 7-continued

| | | | Outcomes Variables 30 days Post Injury | | | | |
|---|---|---|---|---|---|---|---|
| Lower Moderate | 8 | 11.4 | 4 | 18.2 | | 1.65 | 0.63, 4.29 |
| Upper Moderate | 7 | 10.0 | 30.0 | 0 | 0 | 18.2 | |
| Lower Good | 3 | 4.3 | | 0 | 0 | | |
| Upper Good | 3 | 4.3 | | 0 | 0 | | |

| | | | Disability Rating Score | | | | |
|---|---|---|---|---|---|---|---|
| Index GCS = 4-8 | n | Mean | 95% Confidence Interval | | n | Mean | 95% Confidence Interval |
| Employ | 46 | 2.7 | 2.4, 2.9 | | 9 | 2.4 | 1.9, 3.0 |
| Function | 46 | 2.9 | 2.3, 3.5 | | 9 | 1.8 | 0.7, 2.8 |
| Total DRS | 45 | 10.7 | 8.0, 13.4 | | 9 | 4.4 | 2.8, 6.1 |
| Index GCS = 9-12 | | | | | | | |
| Employ | 15 | 1.8 | 1.1, 2.5 | | 6 | 3 | — |
| Function | 15 | 1.5 | 0.5, 2.6 | | 6 | 3.8 | 2.6, 5.1 |
| Total DRS | 15 | 5 | 1.6, 8.4 | | 6 | 12.7 | 7.0, 18.4 |
| | | | Duration of Coma (days) | | | | |
| Initial GCS = 4-8 | 55 | 10.11 | 7.7, 12.5 | | 16 | 3.9 | 2.5, 5.4 |
| Initial GCS = 9-12 | 20 | 4.1 | 1.4, 6.8 | | 7 | 6.1 | 0, 13.2 |
| | | | Duration of Post-Traumatic Amnesia (days) | | | | |
| Initial GCS = 4-8 | 37 | 18.6 | 15.2, 22.0 | | 9 | 12.8 | 5.2, 20.4 |
| Initial GCS = 9-12 | 15 | 10.7 | 6.2, 15.3 | | 3 | 18.3 | 0, 46.9 |

*Analyses of intention to treat;
Analyses of treatment received, one patient died prior to receiving study drug All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of treating a traumatic central nervous system injury in a human subject, comprising administering to said subject an amount of progesterone or synthetic progestin effective to achieve a serum level of progesterone or synthetic progestin of about 100 ng/ml to about 1600 ng/ml.

2. The method of claim 1, comprising parenterally administering said progesterone or synthetic progestin.

3. The method of claim 1, comprising administering said progesterone or synthetic progestin by intravenous infusion.

4. The method of claim 1, wherein progesterone is administered.

5. The method of claim 1, wherein synthetic progestin is administered.

6. The method of claim 1, wherein said amount is effective to achieve a serum level of progesterone or synthetic progestin of about 100 ng/ml to about 1000 ng/ml.

7. The method of claim 1, wherein said amount is effective to achieve a serum level of progesterone or synthetic progestin of about 200 ng/ml to about 450 ng/ml.

8. The method of claim 1, wherein said amount is effective to achieve a serum level of progesterone or synthetic progestin of about 350 ng/ml to about 450 ng/ml.

9. The method of claim 1, wherein said progesterone or synthetic progestin is administered at a rate of about 0.1 mg/kg/hr to about 7 mg/kg/hr, based on the subject's body weight.

10. The method of claim 1, wherein said progesterone or synthetic progestin is administered at a rate of about 0.5 mg/kg/hr, based on the subject's body weight.

11. The method of claim 1, wherein said progesterone or synthetic progestin is administered at a rate of about 12 mg/kg/day, based on the subject's body weight.

12. The method of claim 1, wherein said progesterone or synthetic progestin is administered within 24 hours of the central nervous system injury.

13. The method of claim 1, wherein said progesterone or synthetic progestin is administered within 8 hours of the central nervous system injury.

14. The method of claim 1, wherein said progesterone or synthetic progestin is administered within 4 hours of the central nervous system injury.

15. A method of reducing or preventing neurodegeneration following a traumatic central nervous system injury in a human subject, comprising administering to said subject an effective amount of progesterone or synthetic progestin.

16. A method of effecting neuroprotection in a human subject in need thereof, comprising administering to said subject an effective amount of progesterone or synthetic progestin.

17. A method of treating a traumatic central nervous system injury in a human subject, comprising administrating to said subject an amount of progesterone or synthetic progestin effective to achieve a serum level of progesterone of synthetic progestin of about 100 ng/ml to about 2000 ng/ml.

* * * * *

UNITED STATES PATENT AND TRADEMARK OFFICE
CERTIFICATE OF CORRECTION

| | | |
|---|---|---|
| PATENT NO. | : 8,455,468 B2 | |
| APPLICATION NO. | : 13/045180 | |
| DATED | : June 4, 2013 | |
| INVENTOR(S) | : Stuart W. Hoffman et al. | |

It is certified that error appears in the above-identified patent and that said Letters Patent is hereby corrected as shown below:

In the Specification

Column 1, line 21, please delete the following paragraph:

"This invention was made with United States Government support under 1R01 N5 39097-01A1 awarded by the National Institute of Neurological Disorders and Stroke (NINDS), National Institutes of Health. The United States Government has certain rights in this invention."

and insert the following paragraph:

-- This invention was made with government support under 1R01 N5 39097-01A1 awarded by the National Institute of Neurological Disorders and Stroke (NINDS) of the National Institutes of Health. The government has certain rights in this invention. --

Signed and Sealed this
Tenth Day of June, 2014

Michelle K. Lee
*Deputy Director of the United States Patent and Trademark Office*